US007824878B2

(12) United States Patent
Charm et al.

(10) Patent No.: US 7,824,878 B2
(45) Date of Patent: *Nov. 2, 2010

(54) SENSITIVE METHOD FOR DETECTING LOW LEVELS OF ATP

(75) Inventors: Stanley E. Charm, Boston, MA (US); Cheryl B. Francisco, Assonet, MA (US); Robert J. Markovsky, Brentwood, NH (US); Robert S. Salter, Reading, MA (US); Steven J. Saul, Arlington, MA (US)

(73) Assignee: Charm Sciences, Inc., Lawrence, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/319,602

(22) Filed: Jan. 9, 2009

(65) Prior Publication Data

US 2009/0148852 A1    Jun. 11, 2009

Related U.S. Application Data

(63) Continuation of application No. 11/141,076, filed on May 31, 2005, now Pat. No. 7,494,781, which is a continuation-in-part of application No. 10/843,495, filed on May 11, 2004, now Pat. No. 7,132,249.

(51) Int. Cl.
*C12Q 1/66* (2006.01)
(52) U.S. Cl. .......................................................... 435/8
(58) Field of Classification Search ...................... 435/8
See application file for complete search history.

(56) References Cited

U.S. PATENT DOCUMENTS

| | | |
|---|---|---|
| 3,713,780 A | 1/1973 | Shapiro |
| 3,745,090 A | 7/1973 | Chapelle et al. |
| 3,871,767 A | 3/1975 | Holm-Hansen et al. |
| 3,971,703 A | 7/1976 | Picciolo et al. |
| 4,099,920 A | 7/1978 | Heiss |
| 4,150,950 A | 4/1979 | Takeguchi et al. |
| 4,303,752 A | 12/1981 | Kolehmainen et al. |
| 4,312,950 A | 1/1982 | Snyder et al. |
| 4,353,868 A | 10/1982 | Joslin et al. |
| 4,409,988 A | 10/1983 | Greenspan |
| 4,707,450 A | 11/1987 | Nason |
| 4,770,853 A | 9/1988 | Bernstein |
| 4,806,415 A | 2/1989 | Fossati |
| 5,004,684 A | 4/1991 | Simpson et al. |
| 5,094,939 A | 3/1992 | Okada et al. |
| 5,223,402 A | 6/1993 | Abbas et al. |
| 5,238,649 A | 8/1993 | Nason |
| 5,266,266 A | 11/1993 | Nason |
| 5,283,179 A | 2/1994 | Wood |
| 5,366,867 A | 11/1994 | Kawakami et al. |
| 5,374,535 A | 12/1994 | Zomer et al. |
| 5,583,024 A | 12/1996 | McElroy et al. |
| 5,618,682 A | 4/1997 | Scheirer |
| 5,700,645 A | 12/1997 | Pahuski et al. |
| 5,736,351 A | 4/1998 | Miller et al. |
| 5,744,320 A | 4/1998 | Sherf et al. |
| 5,827,675 A | 10/1998 | Skiffington et al. |
| 5,905,029 A | 5/1999 | Andreotti et al. |
| 5,908,751 A | 6/1999 | Higo et al. |
| 5,916,802 A | 6/1999 | Andreotti |
| 5,965,453 A | 10/1999 | Skiffington et al. |
| 6,180,395 B1 | 1/2001 | Skiffington et al. |
| 6,265,177 B1 | 7/2001 | Squirrell et al. |
| 6,503,723 B1 | 1/2003 | van Lune et al. |
| 6,660,489 B2 | 12/2003 | Schrecengost et al. |
| 6,812,012 B1 | 11/2004 | Hattori et al. |
| 7,132,249 B1 * | 11/2006 | Salter et al. ................... 435/8 |
| 7,494,781 B1 * | 2/2009 | Charm et al. ................ 435/8 |
| 2003/0104507 A1 | 6/2003 | Wood et al. |

FOREIGN PATENT DOCUMENTS

| | | |
|---|---|---|
| EP | 0155747 A1 | 9/1985 |
| EP | 0309429 A2 | 3/1989 |
| EP | 1041151 A1 | 10/2000 |
| JP | 7-59555 | 3/1995 |
| WO | WO-90/04647 | 5/1990 |
| WO | WO-92/20781 | 11/1992 |
| WO | WO-95/07457 | 3/1995 |
| WO | WO-95/25948 | 9/1995 |
| WO | WO-96/14570 | 5/1996 |
| WO | WO-97/23596 | 7/1997 |
| WO | WO-02/066671 A2 | 8/2002 |

OTHER PUBLICATIONS

Philip E. Stanley, Extraction of Adenosine Triphosphate from Microbial and Somatic Cells, Methods in Enzymology, 1986 pp. 14-22, vol. 133, Academic Press Inc, United States.
Sharon R. Ford & Franklin R. Leach, Improvments in the Application of Firefly Luciferase Assays, Methods in Molecular Biology, Bioluminescence Methods and Protocols, pp. 3-20, vol. 102, Humana Press, Totowa, New Jersey.
A. Lundin, Extraction and Automatic Luminometric Assay of ATP, ADP and AMP, Analytical Applications of Bioluminescence and Chemiluminescence, 1984, pp. 491-501, Academic Press Inc., Harcourt Brace Jovanovic Publishers, New York, United States.
Maj-Rita Siro, Henrik Romar & Timo Lov Gren, Continuous Flow Method for Extraction and Bioluminescence Assay of ATP in Baker's Yeast, European Journal of Applied Microbiology and Biotechnology, 1982, pp. 258-264, vol. 15, Springer-Veriag, Finland.
Larry J. Kricka & Marlene Deluca, Effect of Solvents on the Catalytic Activity of Firefly Luciferase, Archives of Bio-Chemistry and Bio-Physics, 1982, pp. 674-681, vol. 217, No. 2, Academic Press Inc., United States.
W.D. McElroy & H.H. Seliger, Mechanisms of Bioluminescent Reactions, A Symposium on Light and Life, 1961, pp. 219-257, The Johns Hopkins Press, United States.

* cited by examiner

*Primary Examiner*—Ralph Gitomer
(74) *Attorney, Agent, or Firm*—Richard J. Long

(57) ABSTRACT

Methods are provided for sensitive detection of adenosine triphosphate (ATP) in samples using the luciferin-luciferase reaction. Aspects include using a pH composition that maximizes a signal to noise ratio. The maximum signal to noise ratio can be particularly useful with recombinant luciferase including recombinant Coleoptera luciferase.

20 Claims, 18 Drawing Sheets

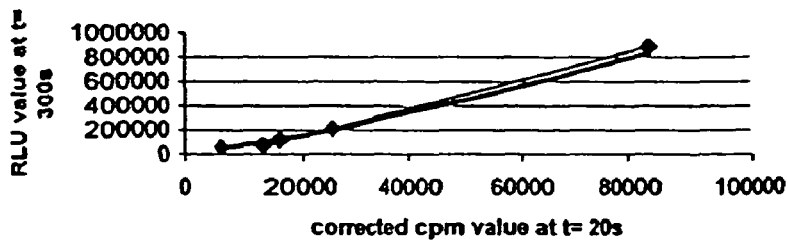
FIGURE 5A: Power Curve Fit
y = 1.2539 * x^(1.183); R = 0.99914
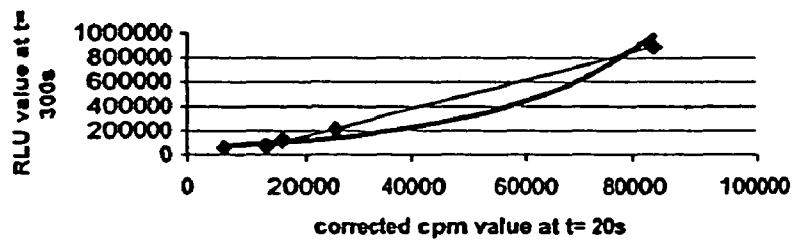
FIGURE 5B: Exponential Curve Fit
y = 59597 * e^(3.3426E-05x); R = 0.99357
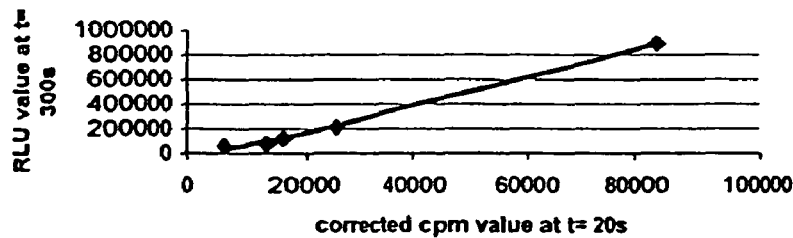
FIGURE 5C: Linear Trend Fit
y = 11.261x - 60594; R = 0.99805
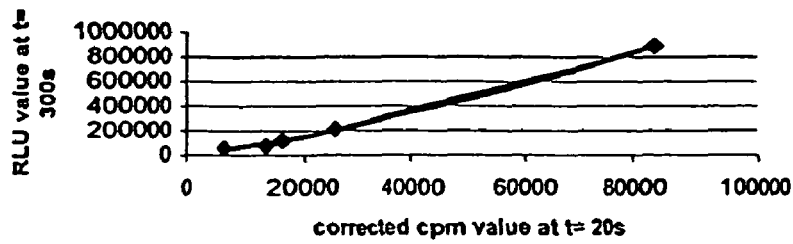
FIGURE 5D: Polynomial Curve Fit
y = 3.9039E-05x^2 + 7.5027x -13737; R = 0.99909

FIGURE 6: POWER CURVE ANALYSIS

|  |  | Col 1 | Col 2 | Col 3 | Col 4 | Col 5 | Col 6 |
|---|---|---|---|---|---|---|---|
| BLANKS | | | | | | | |
| 1 | LUM-T | 3259 | 195540 | 7550 | 64535 | 48513 | -24.8 |
| 2 | #7339 | 3024 | 181440 | 7005 | 53316 | 44403 | -16.7 |
| 3 | (CF=259) | 3818 | 229080 | 8845 | 59786 | 58505 | -2.1 |
| 4 | | 2498 | 149880 | 5787 | 50397 | 35419 | -29.7 |
| 5 | | 3745 | 224700 | 8676 | 68279 | 57184 | -16.2 |
| 6 | | 3042 | 182520 | 7047 | 55257 | 44716 | -19.1 |
| 7 | LUM-T | 3882 | 232920 | 8230 | 56105 | 53729 | -4.2 |
| 8 | #7384 | 2874 | 172440 | 6093 | 52861 | 37648 | -28.8 |
| 9 | (CF=283) | 3387 | 203220 | 7181 | 61378 | 45722 | -25.5 |
| 10 | | 3290 | 197400 | 6975 | 54922 | 44177 | -19.6 |
| 11 | | 3346 | 200760 | 7094 | 62904 | 45068 | -28.4 |
| 12 | | 3240 | 194400 | 6869 | 61180 | 43384 | -29.1 |
| *avg:* | | 3284 | 197025 | 7279 | 58410 | | |
| *stdev:* | | 403 | 24166 | 927 | 5409 | | |
| *avg + 3 stdev* | | 4492 | 269522 | 10059 | 74638 | | |
| 0.005 fmol ATP | | | | | | | |
| 1 | LUM-T | 5506 | 330360 | 12755 | 75704 | 90218 | 19.2 |
| 2 | #7339 | 6420 | 385200 | 14873 | 78572 | 108192 | 37.7 |
| 3 | (CF=259) | 6647 | 398820 | 15398 | 82392 | 112732 | 36.8 |
| 4 | LUM-T | 6056 | 363360 | 12840 | 88060 | 90924 | 3.3 |
| 5 | #7384 | 6373 | 382380 | 13512 | 85657 | 96581 | 12.8 |
| 6 | (CF=283) | 5314 | 318840 | 11266 | 74310 | 77898 | 4.8 |
| 7 | | 7295 | 437700 | 15466 | 93046 | 113321 | 21.8 |
| 8 | | 5448 | 326880 | 11551 | 79136 | 80227 | 1.4 |
| 9 | | 5075 | 304500 | 10760 | 74889 | 73771 | -1.5 |
| *avg:* | | 6015 | 360893 | 13158 | 81307 | | |
| *stdev:* | | 732 | 43923 | 1789 | 6493 | | |

FIGURE 7: POWER CURVE ANALYSIS

0.01 fmol ATP

| | | Col 1 | Col 2 | Col 3 | Col 4 | Col 5 | Col 6 |
|---|---|---|---|---|---|---|---|
| 1 | LUM-T | 6981 | 418860 | 16172 | 111345 | 119464 | 7.3 |
| 2 | #7339 | 7250 | 435000 | 16795 | 118816 | 124929 | 5.1 |
| 3 | (CF=259) | 7343 | 440580 | 17011 | 127213 | 126827 | -0.3 |
| 4 | LUM-T | 8120 | 487200 | 17216 | 126570 | 128634 | 1.6 |
| 5 | #7384 | 9688 | 581280 | 20540 | 142214 | 158514 | 11.5 |
| 6 | (CF=283) | 11045 | 662700 | 23417 | 147097 | 185105 | 25.8 |
| 7 | | 7587 | 455220 | 16086 | 105190 | 118707 | 12.8 |
| 8 | | 9963 | 597780 | 21123 | 165578 | 163851 | -1.0 |
| 9 | | 8307 | 498420 | 17612 | 124534 | 132146 | 6.1 |
| avg: | | 8476 | 508560 | 18441 | 129840 | | |
| stdev: | | 1425 | 85506 | 2598 | 18858 | | |

0.1 fmol ATP

| | | Col 1 | Col 2 | Col 3 | Col 4 | Col 5 | Col 6 |
|---|---|---|---|---|---|---|---|
| 1 | LUM-T | 9747 | 584820 | 22580 | 202721 | 177303 | -12.5 |
| 2 | #7339 | 12527 | 751620 | 29020 | 241183 | 238581 | -1.1 |
| 3 | (CF=259) | 10118 | 607080 | 23439 | 188379 | 185314 | -1.6 |
| avg: | | 10797 | 647840 | 25013 | 210761 | | |
| stdev: | | 1509 | 90563 | 3497 | 27305 | | |

1 fmol ATP

| | | Col 1 | Col 2 | Col 3 | Col 4 | Col 5 | Col 6 |
|---|---|---|---|---|---|---|---|
| 1 | LUM-T | 40352 | 2421120 | 93480 | 935905 | 951964 | 1.7 |
| 2 | #7339 | 36668 | 2200080 | 84945 | 1026771 | 850029 | -17.2 |
| 3 | (CF=259) | 31338 | 1880280 | 72598 | 698156 | 705886 | 1.1 |
| avg: | | 36119 | 2167160 | 83674 | 886944 | | |
| stdev: | | 4532 | 271919 | 10499 | 169690 | | |

FIGURE 8: EXPONENTIAL CURVE ANALYSIS

|  | | Col 1 | Col 2 | Col 3 | Col 4 | Col 5 | Col 6 |
|---|---|---|---|---|---|---|---|
| BLANKS | | | | | | | |
| 1 | LUM-T | 3259 | 195540 | 7550 | 64535 | 74746 | 15.8 |
| 2 | #7339 | 3024 | 181440 | 7005 | 53316 | 73535 | 37.9 |
| 3 | (CF=259) | 3818 | 229080 | 8845 | 59786 | 77707 | 30.0 |
| 4 | | 2498 | 149880 | 5787 | 50397 | 70896 | 40.7 |
| 5 | | 3745 | 224700 | 8676 | 68279 | 77314 | 13.2 |
| 6 | | 3042 | 182520 | 7047 | 55257 | 73627 | 33.2 |
| 7 | LUM-T | 3882 | 232920 | 8230 | 56105 | 76288 | 36.0 |
| 8 | #7384 | 2874 | 172440 | 6093 | 52861 | 71551 | 35.4 |
| 9 | (CF=283) | 3387 | 203220 | 7181 | 61378 | 73924 | 20.4 |
| 10 | | 3290 | 197400 | 6975 | 54922 | 73469 | 33.8 |
| 11 | | 3346 | 200760 | 7094 | 62904 | 73731 | 17.2 |
| 12 | | 3240 | 194400 | 6869 | 61180 | 73236 | 19.7 |
| avg: | | 3284 | 197025 | 7279 | 58410 | | |
| stdev: | | 403 | 24166 | 927 | 5409 | | |
| avg + 3 stdev | | 4492 | 269522 | 10059 | 74638 | | |
| 0.005 fmol ATP | | | | | | | |
| 1 | LUM-T | 5506 | 330360 | 12755 | 75704 | 87380 | 15.4 |
| 2 | #7339 | 6420 | 385200 | 14873 | 78572 | 93110 | 18.5 |
| 3 | (CF=259) | 6647 | 398820 | 15398 | 82392 | 94591 | 14.8 |
| 4 | LUM-T | 6056 | 363360 | 12840 | 88060 | 87601 | -0.5 |
| 5 | #7384 | 6373 | 382380 | 13512 | 85657 | 89385 | 4.4 |
| 6 | (CF=283) | 5314 | 318840 | 11266 | 74310 | 83563 | 12.5 |
| 7 | | 7295 | 437700 | 15466 | 93046 | 94784 | 1.9 |
| 8 | | 5448 | 326880 | 11551 | 79136 | 84278 | 6.5 |
| 9 | | 5075 | 304500 | 10760 | 74889 | 82302 | 9.9 |
| avg: | | 6015 | 360893 | 13158 | 81307 | | |
| stdev: | | 732 | 43923 | 1789 | 6493 | | |

FIGURE 9: EXPONENTIAL CURVE ANALYSIS

|  |  | Col 1 | Col 2 | Col 3 | Col 4 | Col 5 | Col 6 |
|---|---|---|---|---|---|---|---|
| 0.01 fmol ATP | | | | | | | |
| | 1 LUM-T | 6981 | 418860 | 16172 | 111345 | 96812 | -13.1 |
| | 2 #7339 | 7250 | 435000 | 16795 | 118816 | 98639 | -17.0 |
| | 3 (CF=259) | 7343 | 440580 | 17011 | 127213 | 99279 | -22.0 |
| | 4 LUM-T | 8120 | 487200 | 17216 | 126570 | 99890 | -21.1 |
| | 5 #7384 | 9688 | 581280 | 20540 | 142214 | 110366 | -22.4 |
| | 6 (CF=283) | 11045 | 662700 | 23417 | 147097 | 120315 | -18.2 |
| | 7 | 7587 | 455220 | 16086 | 105190 | 96561 | -8.2 |
| | 8 | 9963 | 597780 | 21123 | 165578 | 112314 | -32.2 |
| | 9 | 8307 | 498420 | 17612 | 124534 | 101085 | -18.8 |
| *avg:* | | 8476 | 508560 | 18441 | 129840 | | |
| *stdev:* | | 1425 | 85506 | 2598 | 18858 | | |
| 0.1 fmol ATP | | | | | | | |
| | 1 LUM-T | 9747 | 584820 | 22580 | 202721 | 117331 | -42.1 |
| | 2 #7339 | 12527 | 751620 | 29020 | 241183 | 142338 | -41.0 |
| | 3 (CF=259) | 10118 | 607080 | 23439 | 188379 | 120396 | -36.1 |
| *avg:* | | 10797 | 647840 | 25013 | 210761 | | |
| *stdev:* | | 1509 | 90563 | 3497 | 27305 | | |
| 1 fmol ATP | | | | | | | |
| | 1 LUM-T | 40352 | 2421120 | 93480 | 935905 | 984360 | 5.2 |
| | 2 #7339 | 36668 | 2200080 | 84945 | 1026771 | 762011 | -25.8 |
| | 3 (CF=259) | 31338 | 1880280 | 72598 | 698156 | 526123 | -24.6 |
| *avg:* | | 36119 | 2167160 | 83674 | 886944 | | |
| *stdev:* | | 4532 | 271919 | 10499 | 169690 | | |

FIGURE 10: LINEAR CURVE ANALYSIS

|  | | Col 1 | Col 2 | Col 3 | Col 4 | Col 5 | Col 6 |
|---|---|---|---|---|---|---|---|
| BLANKS | | | | | | | |
| 1 | LUM-T | 3259 | 195540 | 7550 | 64535 | 24424 | -62.2 |
| 2 | #7339 | 3024 | 181440 | 7005 | 53316 | 18294 | -65.7 |
| 3 | (CF=259) | 3818 | 229080 | 8845 | 59786 | 39007 | -34.8 |
| 4 | | 2498 | 149880 | 5787 | 50397 | 4572 | -90.9 |
| 5 | | 3745 | 224700 | 8676 | 68279 | 37103 | -45.7 |
| 6 | | 3042 | 182520 | 7047 | 55257 | 18763 | -66.0 |
| 7 | LUM-T | 3882 | 232920 | 8230 | 56105 | 32088 | -42.8 |
| 8 | #7384 | 2874 | 172440 | 6093 | 52861 | 8022 | -84.8 |
| 9 | (CF=283) | 3387 | 203220 | 7181 | 61378 | 20270 | -67.0 |
| 10 | | 3290 | 197400 | 6975 | 54922 | 17954 | -67.3 |
| 11 | | 3346 | 200760 | 7094 | 62904 | 19291 | -69.3 |
| 12 | | 3240 | 194400 | 6869 | 61180 | 16761 | -72.6 |
| *avg:* | | 3284 | 197025 | 7279 | 58410 | | |
| *stdev:* | | 403 | 24166 | 927 | 5409 | | |
| *avg + 3 stdev* | | 4492 | 269522 | 10059 | 74638 | | |
| 0.005 fmol ATP | | | | | | | |
| 1 | LUM-T | 5506 | 330360 | 12755 | 75704 | 83042 | 9.7 |
| 2 | #7339 | 6420 | 385200 | 14873 | 78572 | 106886 | 36.0 |
| 3 | (CF=259) | 6647 | 398820 | 15398 | 82392 | 112808 | 36.9 |
| 4 | LUM-T | 6056 | 363360 | 12840 | 88060 | 83992 | -4.6 |
| 5 | #7384 | 6373 | 382380 | 13512 | 85657 | 91561 | 6.9 |
| 6 | (CF=283) | 5314 | 318840 | 11266 | 74310 | 66277 | -10.8 |
| 7 | | 7295 | 437700 | 15466 | 93046 | 113573 | 22.1 |
| 8 | | 5448 | 326880 | 11551 | 79136 | 69477 | -12.2 |
| 9 | | 5075 | 304500 | 10760 | 74889 | 60571 | -19.1 |
| *avg:* | | 6015 | 360893 | 13158 | 81307 | | |
| *stdev:* | | 732 | 43923 | 1789 | 6493 | | |

FIGURE 11: LINEAR CURVE ANALYSIS

|  | | Col 1 | Col 2 | Col 3 | Col 4 | Col 5 | Col 6 |
|---|---|---|---|---|---|---|---|
| 0.01 fmol ATP | | | | | | | |
| | 1 LUM-T | 6981 | 418860 | 16172 | 111345 | 121521 | 9.1 |
| | 2 #7339 | 7250 | 435000 | 16795 | 118816 | 128539 | 8.2 |
| | 3 (CF=259) | 7343 | 440580 | 17011 | 127213 | 130965 | 2.9 |
| | 4 LUM-T | 8120 | 487200 | 17216 | 126570 | 133270 | 5.3 |
| | 5 #7384 | 9688 | 581280 | 20540 | 142214 | 170706 | 20.0 |
| | 6 (CF=283) | 11045 | 662700 | 23417 | 147097 | 203104 | 38.1 |
| | 7 | 7587 | 455220 | 16086 | 105190 | 120545 | 14.6 |
| | 8 | 9963 | 597780 | 21123 | 165578 | 177272 | 7.1 |
| | 9 | 8307 | 498420 | 17612 | 124534 | 137735 | 10.6 |
| | avg: | 8476 | 508560 | 18441 | 129840 | | |
| | stdev: | 1425 | 85506 | 2598 | 18858 | | |
| 0.1 fmol ATP | | | | | | | |
| | 1 LUM-T | 9747 | 584820 | 22580 | 202721 | 193679 | -4.5 |
| | 2 #7339 | 12527 | 751620 | 29020 | 241183 | 266201 | 10.4 |
| | 3 (CF=259) | 10118 | 607080 | 23439 | 188379 | 203357 | 8.0 |
| | avg: | 10797 | 647840 | 25013 | 210761 | | |
| | stdev: | 1509 | 90563 | 3497 | 27305 | | |
| 1 fmol ATP | | | | | | | |
| | 1 LUM-T | 40352 | 2421120 | 93480 | 935905 | 992079 | 6.0 |
| | 2 #7339 | 36668 | 2200080 | 84945 | 1026771 | 895974 | -12.7 |
| | 3 (CF=259) | 31338 | 1880280 | 72598 | 698156 | 756929 | 8.4 |
| | avg: | 36119 | 2167160 | 83674 | 886944 | | |
| | stdev: | 4532 | 271919 | 10499 | 169690 | | |

FIGURE 12: POLYNOMIAL CURVE ANALYSIS

| BLANKS | Col 1 | Col 2 | Col 3 | Col 4 | Col 5 | Col 6 |
|---|---|---|---|---|---|---|
| 1 LUM-T | 3259 | 195540 | 7550 | 64535 | 45187 | -30.0 |
| 2 #7339 | 3024 | 181440 | 7005 | 53316 | 40785 | -23.5 |
| 3 (CF=259) | 3818 | 229080 | 8845 | 59786 | 55752 | -6.7 |
| 4 | 2498 | 149880 | 5787 | 50397 | 31020 | -38.4 |
| 5 | 3745 | 224700 | 8676 | 68279 | 54365 | -20.4 |
| 6 | 3042 | 182520 | 7047 | 55257 | 41122 | -25.6 |
| 7 LUM-T | 3882 | 232920 | 8230 | 56105 | 50723 | -9.6 |
| 8 #7384 | 2874 | 172440 | 6093 | 52861 | 33464 | -36.7 |
| 9 (CF=283) | 3387 | 203220 | 7181 | 61378 | 42202 | -31.2 |
| 10 | 3290 | 197400 | 6975 | 54922 | 40542 | -26.2 |
| 11 | 3346 | 200760 | 7094 | 62904 | 41500 | -34.0 |
| 12 | 3240 | 194400 | 6869 | 61180 | 39688 | -35.1 |
| avg: | 3284 | 197025 | 7279 | 58410 | | |
| stdev: | 403 | 24166 | 927 | 5409 | | |
| avg + 3 stdev | 4492 | 269522 | 10059 | 74638 | | |

| 0.005 fmol ATP | | | | | | |
|---|---|---|---|---|---|---|
| 1 LUM-T | 5506 | 330360 | 12755 | 75704 | 88469 | 16.9 |
| 2 #7339 | 6420 | 385200 | 14873 | 78572 | 106695 | 35.8 |
| 3 (CF=259) | 6647 | 398820 | 15398 | 82392 | 111277 | 35.1 |
| 4 LUM-T | 6056 | 363360 | 12840 | 88060 | 89189 | 1.3 |
| 5 #7384 | 6373 | 382380 | 13512 | 85657 | 94940 | 10.8 |
| 6 (CF=283) | 5314 | 318840 | 11266 | 74310 | 75869 | 2.1 |
| 7 | 7295 | 437700 | 15466 | 93046 | 111871 | 20.2 |
| 8 | 5448 | 326880 | 11551 | 79136 | 78260 | -1.1 |
| 9 | 5075 | 304500 | 10760 | 74889 | 71621 | -4.4 |
| avg: | 6015 | 360893 | 13158 | 81307 | | |
| stdev: | 732 | 43923 | 1789 | 6493 | | |

FIGURE 13: POLYNOMIAL CURVE ANALYSIS

|  | Col 1 | Col 2 | Col 3 | Col 4 | Col 5 | Col 6 |
|---|---|---|---|---|---|---|
| 0.01 fmol ATP | | | | | | |
| 1 LUM-T | 6981 | 418860 | 16172 | 111345 | 118060 | 6.0 |
| 2 #7339 | 7250 | 435000 | 16795 | 118816 | 123557 | 4.0 |
| 3 (CF=259) | 7343 | 440580 | 17011 | 127213 | 125465 | -1.4 |
| 4 LUM-T | 8120 | 487200 | 17216 | 126570 | 127281 | 0.6 |
| 5 #7384 | 9688 | 581280 | 20540 | 142214 | 157243 | 10.6 |
| 6 (CF=283) | 11045 | 662700 | 23417 | 147097 | 183888 | 25.0 |
| 7 | 7587 | 455220 | 16086 | 105190 | 117298 | 11.5 |
| 8 | 9963 | 597780 | 21123 | 165578 | 162589 | -1.8 |
| 9 | 8307 | 498420 | 17612 | 124534 | 130808 | 5.0 |
| avg: | 8476 | 508560 | 18441 | 129840 | | |
| stdev: | 1425 | 85506 | 2598 | 18858 | | |
| 0.1 fmol ATP | | | | | | |
| 1 LUM-T | 9747 | 584820 | 22580 | 202721 | 176068 | -13.1 |
| 2 #7339 | 12527 | 751620 | 29020 | 241183 | 237679 | -1.5 |
| 3 (CF=259) | 10118 | 607080 | 23439 | 188379 | 184098 | -2.3 |
| avg: | 10797 | 647840 | 25013 | 210761 | | |
| stdev: | 1509 | 90563 | 3497 | 27305 | | |
| 1 fmol ATP | | | | | | |
| 1 LUM-T | 40352 | 2421120 | 93480 | 935905 | 1037149 | 10.8 |
| 2 #7339 | 36668 | 2200080 | 84945 | 1026771 | 912208 | -11.2 |
| 3 (CF=259) | 31338 | 1880280 | 72598 | 698156 | 741759 | 6.2 |
| avg: | 36119 | 2167160 | 83674 | 886944 | | |
| stdev: | 4532 | 271919 | 10499 | 169690 | | |

FIGURE 14: AVERAGE OF EXPONENTIAL AND POWER CURVES

| BLANKS | | Col 1 | Col 2 | Col 3 | Col 4 | Col 5 | Col 6 |
|---|---|---|---|---|---|---|---|
| 1 | LUM-T | 3259 | 195540 | 7550 | 64535 | 61630 | -4.5 |
| 2 | #7339 | 3024 | 181440 | 7005 | 53316 | 58969 | 10.6 |
| 3 | (CF=259) | 3818 | 229080 | 8845 | 59786 | 68106 | 13.9 |
| 4 | | 2498 | 149880 | 5787 | 50397 | 53157 | 5.5 |
| 5 | | 3745 | 224700 | 8676 | 68279 | 67249 | -1.5 |
| 6 | | 3042 | 182520 | 7047 | 55257 | 59172 | 7.1 |
| 7 | LUM-T | 3882 | 232920 | 8230 | 56105 | 65008 | 15.9 |
| 8 | #7384 | 2874 | 172440 | 6093 | 52861 | 54599 | 3.3 |
| 9 | (CF=283) | 3387 | 203220 | 7181 | 61378 | 59823 | -2.5 |
| 10 | | 3290 | 197400 | 6975 | 54922 | 58823 | 7.1 |
| 11 | | 3346 | 200760 | 7094 | 62904 | 59399 | -5.6 |
| 12 | | 3240 | 194400 | 6869 | 61180 | 58310 | -4.7 |
| avg: | | 3284 | 197025 | 7279 | 58410 | | |
| stdev: | | 403 | 24166 | 927 | 5409 | | |
| avg + 3 stdev | | 4492 | 269522 | 10059 | 74638 | | |

| 0.005 fmol ATP | | | | | | | |
|---|---|---|---|---|---|---|---|
| 1 | LUM-T | 5506 | 330360 | 12755 | 75704 | 88799 | 17.3 |
| 2 | #7339 | 6420 | 385200 | 14873 | 78572 | 100651 | 28.1 |
| 3 | (CF=259) | 6647 | 398820 | 15398 | 82392 | 103661 | 25.8 |
| 4 | LUM-T | 6056 | 363360 | 12840 | 88060 | 89262 | 1.4 |
| 5 | #7384 | 6373 | 382380 | 13512 | 85657 | 92983 | 8.6 |
| 6 | (CF=283) | 5314 | 318840 | 11266 | 74310 | 80730 | 8.6 |
| 7 | | 7295 | 437700 | 15466 | 93046 | 104053 | 11.8 |
| 8 | | 5448 | 326880 | 11551 | 79136 | 82253 | 3.9 |
| 9 | | 5075 | 304500 | 10760 | 74889 | 78036 | 4.2 |
| avg: | | 6015 | 360893 | 13158 | 81307 | | |
| stdev: | | 732 | 43923 | 1789 | 6493 | | |

FIGURE 15: AVERAGE OF EXPONENTIAL AND POWER CURVES

|  | Col 1 | Col 2 | Col 3 | Col 4 | Col 5 | Col 6 |
|---|---|---|---|---|---|---|
| 0.01 fmol ATP | | | | | | |
| 1 LUM-T | 6981 | 418860 | 16172 | 111345 | 108138 | -2.9 |
| 2 #7339 | 7250 | 435000 | 16795 | 118816 | 111784 | -5.9 |
| 3 (CF=259) | 7343 | 440580 | 17011 | 127213 | 113053 | -11.1 |
| 4 LUM-T | 8120 | 487200 | 17216 | 126570 | 114262 | -9.7 |
| 5 #7384 | 9688 | 581280 | 20540 | 142214 | 134440 | -5.5 |
| 6 (CF=283) | 11045 | 662700 | 23417 | 147097 | 152710 | 3.8 |
| 7 | 7587 | 455220 | 16086 | 105190 | 107634 | 2.3 |
| 8 | 9963 | 597780 | 21123 | 165578 | 138082 | -16.6 |
| 9 | 8307 | 498420 | 17612 | 124534 | 116616 | -6.4 |
| avg: | 8476 | 508560 | 18441 | 129840 | | |
| stdev: | 1425 | 85506 | 2598 | 18858 | | |
| 0.1 fmol ATP | | | | | | |
| 1 LUM-T | 9747 | 584820 | 22580 | 202721 | 147317 | -27.3 |
| 2 #7339 | 12527 | 751620 | 29020 | 241183 | 190460 | -21.0 |
| 3 (CF=259) | 10118 | 607080 | 23439 | 188379 | 152855 | -18.9 |
| avg: | 10797 | 647840 | 25013 | 210761 | | |
| stdev: | 1509 | 90563 | 3497 | 27305 | | |
| 1 fmol ATP | | | | | | |
| 1 LUM-T | 40352 | 2421120 | 93480 | 935905 | 968162 | 3.4 |
| 2 #7339 | 36668 | 2200080 | 84945 | 1026771 | 806020 | -21.5 |
| 3 (CF=259) | 31338 | 1880280 | 72598 | 698156 | 616005 | -11.8 |
| avg: | 36119 | 2167160 | 83674 | 886944 | | |
| stdev: | 4532 | 271919 | 10499 | 169690 | | |

SENSITIVE METHOD FOR DETECTING LOW LEVELS OF ATP

REFERENCE TO PRIOR APPLICATIONS

This application is a continuation of U.S. application Ser. No. 11/141,076, filed in May 31, 2005 now U.S. Pat. No. 7,494,781, which in turn is a continuation-in-part of U.S. application Ser. No. 10/843,495, filed May 11, 2004 now U.S. Pat. No. 7,132,249, incorporated herein by this reference.

FIELD

The field involved is detection of adenosine triphosphate (ATP) for hygiene monitoring.

BACKGROUND

Determination of cleanliness in industrial, health care and other settings is important for maintaining good hygiene and sanitation. For example, the surfaces of equipment used for food handling, storage or processing are major sources of microbial and allergen contamination. Microbial contamination can lead to decreased shelf life of products and, if pathogens are present, transmission of disease. Similarly, unexpected allergens on food contact surfaces may contaminate food. Such contamination has the potential to cause adverse reactions, such as an allergic reaction including hives, anaphylaxis and death, in sensitive people who consume or otherwise contact the contaminated food.

Microbial culturing can be used to determine the presence of microorganisms. Culturing, however, is time consuming and, therefore, the necessary "real time" feedback to sanitation and food preparation personnel may not be available. As a result, food exposed to surfaces that are later found to contain potentially harmful microorganisms could enter the food supply.

During the 1990's various rapid and efficient test methods and devices were developed for the detection of contamination on surfaces. Some of these methods do not detect microbes directly but instead use markers such as adenosine triphosphate (ATP) that are indicative of the presence of microbes or residual food contamination of a surface. One such apparatus is the POCKETSWAB-PLUS (POCKETSWAB is a registered trademark of Charm Sciences, Inc. of Lawrence, Mass.), which rapidly and efficiently detects ATP on surfaces. The POCKETSWAB apparatus detects ATP through the reaction of luciferin and luciferase in the presence of ATP to generate luminescence (light). Luminescence can be measured using a luminometer. Such ATP detection systems generally provide the user with an average reading of relative light units (RLU's) over a time period, for example 5 seconds.

Also during the late 1990's, allergen tests were developed to detect allergenic components of foods. These tests are typically in the ELISA (enzyme linked immunosorbent assay) format and require 30 minutes or more to obtain a result. ELISA allergen tests have generally been more sensitive for detecting allergenic food residues than previously available ATP tests such as the POCKETSWAB.

Maximizing the sensitivity of ATP detection assays and systems, particularly single service ATP detection assays, could expand their usefulness. For example, a sensitive ATP detection system could be used to rapidly screen a surface for food residue at the level of allergen test detection. Regulations require sensitivity of 5 parts per million peanut residue for tests that detect peanut allergens.

BRIEF DESCRIPTION OF THE FIGURES

FIG. 1A shows the swab removed from the test device and FIG. 1B shows the swab in a pre-use position within the device.

FIGS. 5A, 5B, 5C and 5D show various curve fits to predict extended RLU counts from 20 second RLU counts as follows: 5A (Power Curve Fit), 5B (Exponential Curve Fit), 5C (Linear Trend Fit) and 5D (Polynomial Curve Fit).

FIG. 6 shows sample data from a Power Curve Fit analysis using two different luminometers at zero fmol ATP and 0.005 fmol ATP.

FIG. 7 shows sample data from a Power Curve Fit analysis using two different luminometers at 0.01 fmol ATP, 0.1 fmol ATP and 1 fmol ATP.

FIG. 8 shows sample data from an Exponential Curve Fit analysis using two different luminometers at zero fmol ATP and 0.005 fmol ATP.

FIG. 9 shows sample data from an Exponential Curve Fit analysis using two different luminometers at 0.01 fmol ATP, 0.1 fmol ATP and 1 fmol ATP.

FIG. 10 shows sample data from a Linear Curve Fit analysis using two different luminometers at zero fmol ATP and 0.005 fmol ATP.

FIG. 11 shows sample data from a Linear Curve Fit analysis using two different luminometers at 0.01 fmol ATP, 0.1 fmol ATP and 1 fmol ATP.

FIG. 12 shows sample data from a Polynomial Curve Fit analysis using two different luminometers at zero fmol ATP and 0.005 fmol ATP.

FIG. 13 shows sample data from a Polynomial Curve Fit analysis using two different luminometers at 0.01 fmol ATP, 0.1 fmol ATP and 1 fmol ATP.

FIG. 14 shows sample data from an average of Exponential and Power Curve Fit analysis using two different luminometers at zero fmol ATP and 0.005 fmol ATP.

FIG. 15 shows sample data from an average of Exponential and Power Curve Fit analysis using two different luminometers at 0.01 fmol ATP, 0.1 fmol ATP and 1 fmol ATP.

SUMMARY

Figure 1:
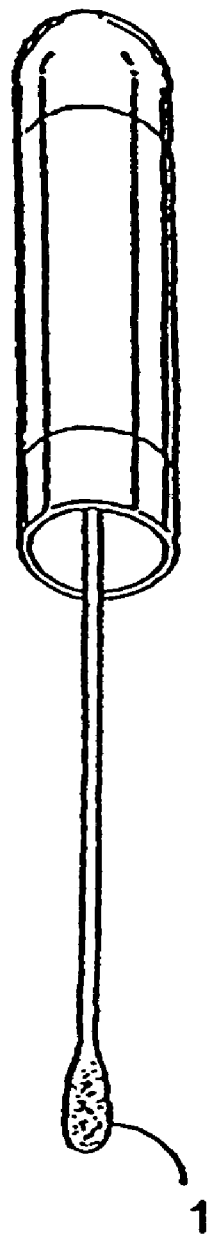
FIGS. 1A and 1B are schematic views of a sampling test device.
Figure 1:
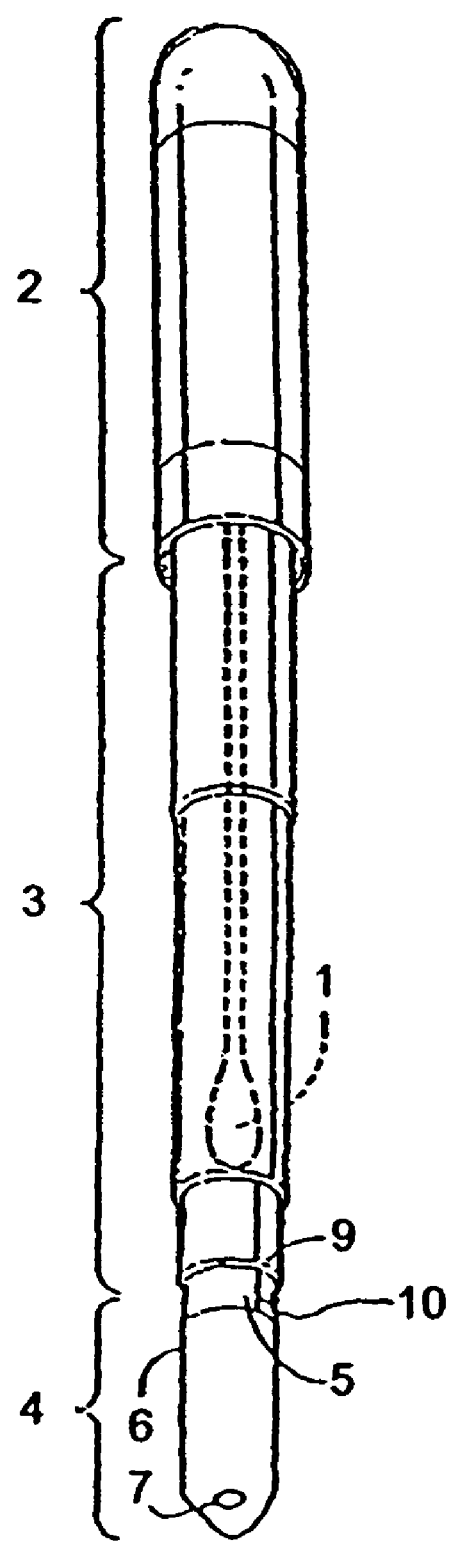

Various aspects involve methods, devices and systems for improved detection of ATP in a sample. In an embodiment adding a test sample to a solution creates a first admixture and then admixing said first admixture with reagents, such as luciferin and luciferase reagents, forms a second admixture. In addition to luciferin and luciferase, said second admixture can include at least one buffer and co-factors, such as magnesium, for the luciferin-luciferase reaction. The second admixture can also include one or more detergents. In many cases, the detergent, for example benzalkonium chloride, Triton X-100 or similar such detergents alone or in combination, will be provided in the solution to which the test sample is added to form the first admixture. If detergents are provided, the percentages of each detergent relative to buffer, can be, for example, in the range of about 0.003% to about 0.1%, for example in the range of 0.003% to about 0.01%, for example 0.005%. The second admixture can also include at least one co-factor for the luciferin-luciferase-ATP reaction, for example magnesium. In an example, the buffer, for example a phosphate buffer including partly, mostly or exclusively dibasic phosphate, is provided at a molar concentration of less than about 100 millimolar. Other possible buffers include Bis-Tris and Bis-Tris Propane.

The reaction resulting from the creation of the second admixture generates luminescence. The luminescence generated is detected and used as an indication of sample ATP. It will be appreciated that although we generally refer to the solution as including the buffer and detergent in liquid form and the reagent, or reagent composition, as including the luciferin-luciferase in solid form, such as in a tablet, it is also possible to have luciferin-luciferase in liquid form. Similarly, the buffer and detergent ingredients can be provided in solid form to be rehydrated during, or prior to, testing. Utilizing solid material, for example in tablet form, that is later hydrated may allow all reagents to be stored together thereby avoiding the first admixture.

In one aspect, enhanced ATP sensitivity can be achieved when the luciferin-luciferase-ATP reaction occurs at pH other than the pH of maximum luminescence output. That pH can change, for example depending on the type of luciferase used. For example, with certain recombinant luciferase, maximum light output occurs at around pH 7.5 to pH 7.8. However, increased sensitivity can be achieved at pH less than 7.8, for example about 6.3 to about 7.2, for example about 6.5 to about 7.2 or about pH 6.5 to about pH 6.9. Such enhanced sensitivity, rather than involving maximum luminescence output, involves maximizing the signal to noise ratio by decreasing background readings.

Another aspect involves detecting the total light generated from the ATP reaction during a relatively short time, for example about 5 seconds to about 30 seconds, and extrapolating, for example using a regression formula, to predict the light that would be generated over a longer period of time, for example 5 minutes. The combination of methods for detection of luminescence and prediction of extended counts, with the methods for enhancing ATP sensitivity using, for example relatively low pH, optimum buffers and detergents at optimum concentrations can provide increased ATP sensitivity, for example at the level useful for allergen detection.

Other aspects include using improved detection of ATP as an indicator of possible allergen contamination or as an indicator of relatively low levels of microbial contamination.

Another aspect includes an easy to use all-in-one device for ATP detection at improved sensitivity levels. Such a device can include a longitudinal housing having a one end and another end and a moveable probe within the housing to collect a test sample. A transparent closed bottom end can extend from the one end of the housing for use to detect the luminescence generated from a test sample of a variety of possible volumes, for example 300 microliters. In an of an all-in-one device a moveable probe is arranged to puncture at least one membrane seal which separates various mixtures, for example a solution from a reagent composition. In another example, the membrane seals surround a chamber in which a solution, or, alternatively, a reagent composition, can be provided.

Another aspect includes improved hygiene monitoring through improved methods for measuring and interpreting luminescence output. In one such method, a sample is added to reagents, such as luciferin-luciferase, that generates luminescence in the presence of ATP. The sample and reagents are combined in a container that is inserted into a luminescence detector, such as a photomultiplier based detector, a photodiode based detector or other detectors capable of measuring luminescence. The luminescence detector detects, quantifies, and stores in memory, the total luminescence output from the sample and reagents, with or without the background subtracted, during a predetermined period of time. Total luminescence generated is detected, for example by detecting RLU's generated per second and adding together the total RLU's generated, for example, during a time period of about 5 seconds to about 60 seconds or more, for example about 20 seconds. That total can be used as the result or, alternatively, used to predict the total luminescence that would be generated during a longer period of time, for example during 5 minutes. By using a shorter count, for example, a 20 second count, to accurately extrapolate (predict) a longer count, such as a 5 minute count, sensitivity can be increased. The program used for calculating or predicting total RLU's can be internal to the luminescence detector or external, for example in an accessory computer.

To predict the RLU's that would be generated during, for example, a 5 minute count, a variety of possible formulas can be used including a linear or non-linear regression formula. Examples of such non-linear regression formulas include power curve formulas, exponential curve formulas and polynomial curve formulas. In addition, it is possible to predict using the average results from two or more formulas.

The described method for using RLU totals, rather than RLU averages, and predicting extended time RLU totals from shorter time RLU totals, can be used in combination with the herein described pH conditions and/or reagents, such as the particular types of buffers and/or detergents at the relevant concentrations. Using such combinations of RLU totaling can increase ATP sensitivity to the level required for indication of allergen potential.

Examples of potential applications for the herein described sensitive ATP detection methods, devices and systems include testing water, such as spring water or other bottled water, for contamination and testing water to be used by pharmaceutical companies to meet USPC standards. Another possible application is in dairies that share production lines between dairy and non-dairy items and where dairy residue in the non-dairy materials is an allergenic concern. Still another application is as an indirect method for screening a surface for allergenic foods; a positive result would tell the user that food residue ATP may exist at the level of allergen test detection. Another potential application includes a test to detect the potential for contamination on surfaces or, for example, in drinking water. In one embodiment, a sample, for example a water sample, is filtered to concentrate organic matter and then the concentrate is tested for the presence of ATP.

Another aspect is a screening test that can be used alone or in a testing system in combination with a confirmatory specific allergen detection test, such as an antibody-binding assay, for detection of specific allergens such as peanut allergen. Food residue related ATP that may be detected using this method include, without limitation, peanut, soy nut, peanut butter, almond, walnut, pecan, egg white, whole egg, pasteurized whole milk, whole wheat flour, white flour, raw clams, raw shrimp, salmon, sunflower seeds, sesame seeds, powdered milk, soy flour and ultra high temperature milk.

Use of such an ATP detection method for allergen detection, alone or in combination with specific allergen tests, can reduce testing costs and testing time by allowing rapid, inexpensive surface screening. Such a test would also be useful in expediting remediation of suspect surfaces. After surface cleanliness has been determined with the ATP test system, confirmation of either lack of, or presence of, specific allergen can be made with a specific allergen test.

DEFINITIONS

Within this application we use the term "buffer" both in accordance with its ordinary meaning and with an additional meaning. The ordinary meaning in the art is a solution that resists change in pH when acid or alkali is added. We also use the term "buffer" to refer to solutions, or other organizations of material including solids, powder, and tablets that may be later reconstituted.

DETAILED DESCRIPTION

Embodiments include a method for optimizing or increasing the sensitivity of ATP detection systems. The method is useful as a technique to increase ATP sensitivity of an ATP detection test device or system independent of the concentrations of costly components such as luciferin or luciferase. In addition to increasing test costs, increasing the concentrations of luciferin and/or luciferase can increase the background of the test system. Increasing the background can cause misleading results by decreasing the signal to noise ratio. With high background, or noise, a negative sample may generate a reading unrelated to the amount of contamination detected and, thereby, decreasing the efficiency of the system.

In some embodiments the ATP detection method involves a test device with a foam tip, or other absorbent type swab or wand for sample uptake from the surface to be monitored. The swab can be pre-moistened with a wetting solution, for example, with the same solution used elsewhere in the system such as a buffering-ATP releasing solution (BAR solution). After sample uptake (for example by absorption through swabbing a surface, pipetting onto the swab or dipping the swab into a sample) onto a swab, the swab is used to contact the sample with the various components of the device. In an embodiment, the swab first contacts a BAR solution and then contacts a luciferin/luciferase reagent composition.

In one embodiment, luciferin is purified beetle D-Luciferin free acid from Regis Technologies, Inc., Catalog #360100 and recombinant-luciferase (r-luciferase) is from PROMEGA (cloned gene from *Photinus pyralis*) (Promega is a registered trademark of Promega Corporation, Madison, Wis.). In an example, luciferase had a specific activity of $3.9 \times 10^{10}$ relative light units per mg protein (sample minimum specification of $2.0 \times 10^{10}$ relative light units per mg protein). Although many specific examples described herein include the above described recombinant luciferase from PROMEGA a variety of natural and recombinant luciferases are known in the art and can be usefully employed in various aspects and embodiments including those described in U.S. Patent application number 2005/0079567 A1, Choi et al., published Apr. 14, 2005; U.S. Pat. No. 6,812,012, Hattori et al., issued Nov. 2, 2004; U.S. Pat. No. 6,265,177 B1, Squirrell et al., issued Jul. 24, 2001; U.S. Pat. No. 5,744,320, Sherf et al., issued Apr. 29, 1998; and U.S. Pat. No. 5,583,024, McElroy et al., issued Dec. 10, 1996, the teachings of all being incorporated herein by this reference. For example, in one embodiment of the disclosure, the luciferase may be a recombinant expression of Coleoptera luciferase as presented in McElroy et al., wherein the Coleoptera luciferase catalyzes the oxidation of Coleoptera luciferin to yield light. The Coleoptera luciferase may be produced by expressing in a prokaryotic or eukaryotic cell, a lysate of said cell or a cell-free protein translation system a recombinant DNA coding for Coleoptera luciferase, wherein said Coleoptera luciferase catalyzes the oxidation of Coleoptera luciferin to yield light.

Luciferin and luciferase can be freeze dried together, for example with ATP-free bulking agents and stabilizers or provided separately for later mixing. The reagents can be provided in a tablet or not tableted. Although the ratio of luciferin and/or luciferase to BAR solution can vary, exemplary ratios include a ratio of about 0.07 to about 0.08 micrograms luciferin per microliter BAR solution and about 0.007 to about 0.008 micrograms luciferase per microliter BAR solution. In a specific example, 300 microliters of BAR solution were used. The ratio of luciferase and luciferin can be adjusted to achieve optimum results. For example, the ratio of luciferase to BAR solution can be increased along with, or independently of, increasing the ratio of luciferin to BAR solution. The ratio can also be adjusted in combination with other optimization methods, such as using a regression formula, to achieve optimum results. It is also possible, utilizing the improved methods of reading the luminescence output described herein, to reduce the ratio or amount of luciferase and/or luciferin thereby decreasing the cost per test and the test background.

In an embodiment in which ATP sensitivity is increased without increasing luciferin or luciferase concentrations, the BAR solution is buffer, such as Bis-Tris or phosphate buffer such as a combination of purified water and potassium phosphate, for example, dibasic potassium phosphate. The molarity of the buffer can be adjusted to optimize test sensitivity while providing sufficient buffering capacity to maintain the desired pH of the reaction. For example, concentrations of buffers in the range of about 0.1 millimolar to about 10 millimolar can increase test sensitivity. Buffering capacity, however, will be minimal. Higher concentrations, for example in the range of about 25 millimolar to about 100 millimolar, can also be used to increase the buffering capacity while maintaining high sensitivity. The pH of the buffer can be adjusted to the desired range using, for example, sodium hydroxide or phosphoric acid. One useful phosphate buffer, such as when the sample does not require a lot of buffering for the desired pH range, is known as Butterfield's Buffer. Another useful phosphate buffer utilizes dibasic phosphate and can be combined with a detergent, such as benzalkonium chloride, Triton X-100 or the like. Other useful phosphate buffers include various mono, di and polyphosphates and their various salts for example phosphoric acid and its sodium, potassium or other salts such as monobasic sodium phosphate, dibasic sodium phosphate, tribasic sodium phosphate, pyrophosphoric acid and other salts and polyphosphoric acid and its various salts, Bis-Tris and Bis-Tris Propane, all of which can also be combined with detergents.

Detergents can be included in the BAR solution. Examples of BAR solutions that may be improved with detergents include phosphate buffer, Bis-Tris buffer and Bis-Tris propane buffer. Possible detergents or combinations of detergents are known to those skilled in the art and include nonionic detergents such as Triton X-100, Tween 20, Tween 80, Nonidet P40 and n-Undecyl Beta-D glucopyranoside; zwitterionic detergents such as n-hexadecyl-N, N-dimethyl-3-ammonio-1-propanesulfonate; and cationic detergents such as alkyltrimethylethylammonium bromides, cetyldimethylethylammonium bromide, dodecyltrimethylammonium bromide, and cetyltrimethylammonium bromide. The concentration of detergent solution varies for each type of detergent. In one embodiment a detergent, for example a quaternary ammonium compound such as benzalkonium chloride, is added to the buffer solution. In an embodiment, Triton X-100 is also included. The one or more detergents can each alone or combined have a concentration in the buffer of less than about 0.1%, for example less than about 0.03%. In a specific example, the concentration of benzalkonium chloride was about 0.02% and the concentration of Triton X-100 was about 0.05% in a 50 mM Bis-Tris buffer, pH 6.6. Such detergents at such concentrations can improve test sensitivity.

In a particular embodiment, the BAR solution includes a combination of about 10 millimolar dibasic phosphate buffer combined with about 0.005% benzalkonium chloride. In another embodiment, the BAR solution includes less than about 1.0 millimolar dibasic phosphate buffer, for example about 0.1 to about 0.5 millimolar dibasic phosphate buffer. In a particular embodiment, about 0.2 to about 0.3 millimolar dibasic phosphate buffer is combined with benzalkonium chloride in a ratio of about 99.995% phosphate buffer to about 0.005% benzalkonium chloride, to a total volume of about 300 microliters.

In an example using increased luciferin and/or increased luciferase relative to BAR solution as a method of increasing test sensitivity to ATP, a BAR solution of 3.138% Trizma Base, 3.125% phosphoric acid detergent, 1.344% Tricine, 1.344% Triton X-100 (10% solution) and 0.172% benzalkonium chloride (10% solution) and deionized water was prepared. (Displacement measurements for Trizma base and tricine were used to calculate the volume of deionized water needed.) The molarity of the BAR solution as described above, is greater than about 300 millimolar. The ratio of luciferase to BAR solution was 0.2409 micrograms luciferase per microliter BAR solution and the ratio of luciferin to BAR solution was 0.481 micrograms luciferin per microliter BAR solution. The result, using a five second non-cumulative (average) RLU count was a 100 fold increase in assay sensitivity, as compared with a similar formulation utilizing the Charm POCKETSWAB Plus (POCKETSWAB Plus containing approximately 0.07 luciferin to BAR solution and 0.007 luciferase to BAR solution), allowing detection of 0.05 femtomoles (fmoles) ATP. It will be appreciated that these formulations could also be used with the various improved RLU counting and calculating methods described herein.

An embodiment, using a decrease in luciferase concentration, as compared to the above example and a five second non-cumulative (average) RLU count, demonstrates that by decreasing the molarity of the BAR solution ATP sensitivity may be increased. In this embodiment, BAR solution was water of about pH 6. The ratio of luciferase to BAR solution was 0.0365 micrograms per microliter (less than the 0.2409 micrograms per microliter described in the previous example) and the ratio of luciferin to BAR was about 0.07 micrograms per microliter. The result was a 100 fold increase in assay sensitivity relative to Charm POCKETSWAB Plus (POCKETSWAB Plus containing approximately 0.07 luciferin to BAR solution and 0.007 luciferase to BAR solution), allowing a maximum sensitivity of approximately 0.05 femtomoles ATP. Peanut butter was detectable with a sensitivity of 5 parts per million. This formulation can also be used with the various improved RLU counting and calculating methods described herein.

Other embodiments include using low molarity BAR solutions as a method of increasing test sensitivity to ATP (increasing luminescence output) without increasing luciferin/luciferase ratios relative to BAR solution and with or without the various improved RLU counting and calculating methods described herein. Specific embodiments for providing an increase in ATP sensitivity without relying on changes in luciferin/luciferase ratios relative to BAR solution include utilizing buffers useful in the pH range of about 6.3 to about 7.2, such as phosphate buffer, Bis-Tris, Bis-Tris Propane and the like, alone or in combination with non-ionic or ionic detergents such as benzalkonium chloride and/or Triton X-100 for example with individual detergent concentrations below about 0.5%. The following are examples of possible specific BAR solutions that may be useful; 1) phosphate buffer, for example Butterfield's Buffer (less than 1 millimolar dibasic phosphate); 2) phosphate buffer, for example Butterfield's Buffer containing a detergent, such as a quaternary ammonium compound such as benzalkonium chloride, for example in a concentration less than 0.1%; 3) water pH of about 5.5 to pH of about 6.5; 4) water pH about 5.5 to about 6.5 with detergent such as a quaternary ammonium compound, such as benzalkonium chloride; 5) Tris-tricine buffer; 6) dibasic phosphate buffer; 7) dibasic phosphate buffer, containing a detergent, such as a quaternary ammonium compound, such as benzalkonium chloride, for example in a concentration less than 0.1% with a pH less than about pH 7.2; 8) tricine buffer, for example about 10 millimolar to about 100 millimolar tricine with or without a detergent such as quaternary ammonium compound, such as benzalkonium chloride, for example in a concentration less than 0.1%; and 9) dibasic phosphate buffer, such as Butterfield's Buffer or equivalent, for example with a molarity of about 0.2 mM to about 0.5 mM with or without detergent such as benzalkonium chloride, for example in a ratio of about 99.995% phosphate buffer to about 0.005% benzalkonium chloride, with a pH of about 6.9; 10) Bis-Tris buffer of molarity less than about 100 mM such as about 50 mM with or without detergents such as benzalkonium chloride and/or Triton X-100 or the like and with exemplary individual detergent concentrations below about 0.5% for non-ionic detergents such as Triton X-100 and below about 0.1% for ionic detergents such as benzalkonium chloride; 11) phosphate buffer of molarity less than about 100 mM such as about 50 mM with or without detergents such as benzalkonium chloride and/or Triton X-100 or the like with exemplary individual detergent concentrations below about 0.5% for non-ionic detergents such as Triton X-100 and below about 0.1% for ionic detergents such as benzalkonium chloride.

In one embodiment, using the BAR solution described in 9 above, the pH of the BAR solution is less than about 7.2, approximately pH 6.9. The BAR solution was combined with a luciferin and luciferase reagent composition including other buffers, co-factors and stabilizers well known in the art. Approximately 0.24 millimolar dibasic potassium phosphate was used in the BAR solution and, approximately, 0.03 micrograms glycine (1.4 millimolar when combined with 300 microliter BAR solution) was used in the luciferin and luciferase reagent composition. In such an embodiment, the final reaction pH will be, for example less than about 6.9 and the molar concentration of total buffer, including phosphate and glycine will be less than about 2 millimolar.

In another embodiment the BAR solution was provided within a chamber of a test system, said chamber sealed with at least one, and generally two, puncturable membrane seals. Examples of test systems utilizing such chambers (herein sometimes referred to as niblets) include the POCKETSWAB-Plus, POCKETSWAB Ultra, POCKETH2O, ALLERGIENE, WATERGIENE (Charm Sciences, Inc. Lawrence, Mass.). In some embodiments such test systems may be brought to room temperature prior to use. After sample contact, the swab can be used to puncture the niblet membrane, or membrane seals of a series of niblets, thereby releasing test reagents into a test vial and activating the necessary reagents. Generally, the test vial is a transparent or translucent vial, which permits the passage or emission of generated luminescence, for example, in a bioluminescent assay, and, for example, permits luminescence transmission of from about 300 to 650 nanometers, which is the visible light range. When other reagents within the test vial are dry, such as in tablet or powder form, a desiccant can also be provided within the test vial such as molecular sieve 4×8 mesh desiccant (AGM Container Controls, Inc. Tucson, Ariz.)

Methods and test devices for luminescence based ATP detection require readers, such as photomultiplier based readers generally known as luminometers. Examples of such luminometers include those described in U.S. Pat. No. 6,055,050. The luminometer may be used in combination with a system including reagents for generation of luminescence in the presence of ATP, for example the single service ATP detection device known as the POCKETSWAB and described in U.S. Pat. No. 6,055,050 and further described in U.S. Pat. No. 5,965,453 (Test Apparatus, System and Method for the Detection of Test Samples); U.S. Pat. No. 5,985,675 (Test Device for Detection of an Analyte) and U.S. Reissue patent application Ser. No. 10/014,154; U.S. Pat. No. 6,180,395 (Reagent Chamber for Test Apparatus and Test Apparatus); all of which are incorporated herein by this reference. The luminescence reader may, for example, be in the format of the LUMINATOR-K, LUMINATOR-T, FIREFLY, LUM-96 and NOVALUM readers (Luminator, Firefly, LUM-96 and NovaLum are trademarks of Charm Sciences, Inc.; Lawrence, Mass.) The luminescence reader may also be in the format of any luminescence reading device that detects RLU's such as by using a photodiode, or as with a photomultiplier based luminometer. In these embodiments, the test apparatus provides a user with the luminescence emission count, in RLU's, of a test sample.

In some embodiments the test result is compared with a background. When using an RLU reading as a measure of sample ATP one possible source of background counts is electrical noise. In certain light detection systems such as photomultiplier based systems, a source of background counts may be what is known in the art as "dark counts" resulting from, for example, thermal, chemiluminescent, or fluorescent emissions from test components. It is also possible that background counts result from outside light sources if the light detection mechanism is not contained within a tightly light sealed environment. In well-designed and constructed equipment, such sources of background counts are relatively minimal.

In some embodiments the system includes using a black swab including black swab shaft and/or absorbent tip. Such black swab can be used to reduce the amount of light that is absorbed and/or reflected by the system that does not relate to ATP luminescence from the sample. Another source of background counts is residual ATP present in test reagents. A method for eliminating the impact of background counts is to program the reader to remove background counts from the result. When background counts are deducted, sensitivity of the system is reflected by the signal to noise ratio rather than the total luminescence.

In several embodiments a background is determined for a particular instrument by running multiple tests without sample. In an example, a POCKETSWAB, for example a POCKETSWAB with BAR solution and luciferin/luciferase concentration chosen to be adequately sensitive and cost effective is not contacted with a sample and is instead contacted with only the reagents and solutions of the system and counted on a luminometer ("activated negative swab"). In one particular example 30 activated negative swabs are counted with a 5 minute cumulative count (300 RLU counts per second counts added together). The standard deviation of the counts from 30 negative swabs is determined and used to adjust the background reading to assure a positive test result is not caused by a high background reading. In another example, a certain number of standard deviations, from about 2 standard deviations to about 5 or more, or fractions thereof, are added to the median or average counts. For example, in one embodiment, 2.5 standard deviations are added to the median result of the multiple, for example, 30 readings. In another example, 3 standard deviations are added. The standard deviation adjustment will vary and is at least partially dependent on reagent consistency, and target test specificity and sensitivity.

In another embodiment, 30 activated negative swabs are read on multiple luminometers. The background is set relative to counts of the activated negative swabs on the multiple luminometers.

After calculation, the background can be programmed into a reader. As a sample count proceeds the reader program can compare cumulative readings to the background. In an embodiment, if the cumulative reading becomes greater than the background, then the sample is determined to contain ATP. The background of the reader can be set so that counts above zero indicate a positive result. In another embodiment, counts above a value other than zero indicate a positive result.

Cumulative readings can exceed background at any time up to the maximum predetermined count time, for example 5 minutes. If the maximum predetermined count time is reached, and the cumulative readings have not exceeded the background, the sample is negative. Conversely, for highly contaminated surfaces, cumulative readings can exceed background relatively quickly making it unnecessary to continue with the full 5 minute count.

In another embodiment, the luminometer, for example a luminometer described above, can be optimized by adjusting the luminescence output reading and interpretation, for example by using a cumulative RLU/second reading, a peak RLU reading and/or an integrating RLU/second reading. These readings can be over 5 seconds or, to increase test sensitivity, over an extended period of time such as 10 seconds, 20 seconds or 30 seconds up to 5 minutes or more. This method for optimizing the luminometer can be used alone or in combination with increasing luciferin/luciferase levels and/or improved BAR solutions, as a method for increasing test sensitivity. In addition to the use with photomultiplier based luminometers, or other luminescence output readers, such methods for increasing test sensitivity can be used with other types of light detectors such as photodiodes.

In some embodiments, after contacting the sample with the BAR solution to create a first admixture, the first admixture is contacted with luciferin and luciferase reagents to create a second admixture. The reaction of ATP from the sample with the luciferin/luciferase reagents generates luminescence that is detected by a reader. The reader detects RLU's, for example RLU's emitted per second. Said reader can be programmed to detect RLU's over a period of time ranging from a few seconds, for example 5 seconds, to several minutes, for example 5 or 10 minutes. It will be appreciated by those skilled in the art that a reading of RLU/second is common in the ATP hygiene monitoring industry. It is possible, however, to change the RLU/second to a different RLU per time reading, for example, RLU per one-half second or RLU per 2 seconds.

For example, in a 5 minute count, the reader can take a count of the RLU's emitted from the sample every second generating 300 readings. The total of those 300 readings can be the test result.

In one embodiment, desired ATP sensitivity levels are achieved through optimizing the light output reading and interpretation, for example by using a cumulative or integrated RLU/second reading or a peak RLU reading, over an extended period of time alone or in combination with increasing luciferin/luciferase levels and improving the BAR solution.

Other possible examples include using a reader, or a connected CPU, programmed to: 1) take 300 readings over the course of 5 minutes—of those 300 readings a subset is chosen, for example a subset defined by the highest 100 readings which are accumulated to provide a test result; 2) take 300 readings and determine the highest, or peak, reading and chose a subset of readings chosen by reference to the peak, for example 50 readings prior and 50 readings subsequent to the peak, as the subset to accumulate readings; 3) integrate the counts and the result reflects the area under the integration curve; 4) take the median reading and choose a subset of readings, by reference to the median reading, to use in the result calculation; 5) determine the peak RLU/second reading and using that peak reading as the test result; 6) use a group of peak readings, for example the highest 50 readings to generate the peak reading result and average, accumulate or otherwise manipulate those median reading to arrive at the "peak" readings; and 7) calculate the rate of change of the RLU/second readings over a given period of time and use that rate of change to determine the test result.

In another embodiment the rate of change of the RLU/second (counts per second) readings is determined over a given period of time. That rate of change is used to determine the test result, for example by a software program within the reader or a software program in a separate computer to which reader results are downloaded.

The method of reading results described herein, and the various BAR solutions, can be used with a variety of luminescence generating reagents including chemiluminescent reagents, for example dioxetane derivatives such as those available from APPLIED BIOSYSTEMS (Applied Biosystems is a registered trademark of Perkin-Elmer Corporation, Foster City, Calif.) and bioluminescent reagents, for example those available from PROMEGA. The method can also be used with a variety of luciferases described herein from both natural and recombinant sources including heat and/or detergent stable recombinant luciferase. The insect luciferin can be derived from bioluminescent insects, for example Diptera and Coleoptera. Other insect species that display the phenomena of bioluminescence can also be suitably employed. Including, for example, species from the orders Diptera and Coleoptera, including the families Lampyridae (including genus Photinus) and Elateridae. Using, for example dioxetane derivatives, compounds other than ATP can be detected and used, for example, as markers of contamination.

As described above, we have found that extending the count time beyond 5 seconds, for example to 5 minutes, and accumulating the counts, rather than averaging the counts, provides increased sensitivity as compared to a 5 second average RLU count. It also may be desirable to provide a more rapid result to the user. It might not be practical or desirable to wait one or more minutes for results. In embodiments, results similar to those observed in an extended cumulative count are calculated from counts of a shorter time period, for example counting RLU's per second, for about 5 seconds to about 30 seconds, adding together the RLU per second counts to arrive at the total RLU generated during those times, and then using one of a variety of possible formulas, to predict total counts over an extended longer time. These methods can be used with a variety of ATP detection methods and reagent formulations for example those described heretofore and hereinafter within this application. In these embodiments, sample RLU results, after a brief period of time, for example 5 seconds, 10 seconds, 20 seconds, or 30 seconds, are used to calculate an expected result after, for example 5 minutes. In one example, a regression curve formula is used to calculate an expected 5 minute result from an actual 20 second cumulative RLU result. Examples of useful regression formulas include power curve, exponential curve, polynomial curve and linear trend formulas. Some specific examples include:

1. A power curve method in which $y=1.2539*x^{1.183}$ where y is the result sought (the predicted result after 5 minutes) and x is the 20 second result converted to counts per minute and corrected by reference to a standard LUMINATOR-T.
2. An exponential curve method in which $y=59597*e^{(3.3426E-05x)}$ where y is the result sought (the predicted result after 5 minutes) and x is the 20 second result converted to counts per minute and corrected by reference to a standard LUMINATOR-T.
3. A linear equation method in which $y=60594+11.261x$ where y is the result sought (the predicted result after 5 minutes) and x is the 20 second result converted to counts per minute and corrected by reference to a standard LUMINATOR-T.
4. A polynomial curve method in which $y=-13737+7.5027*x+3.9039E-05x^2$ where y is the result sought (the predicted result after 5 minutes) and x is the 20 second result converted to counts per minute and corrected by reference to a standard LUMINATOR-T In another example, results from two or more regression formulas are averaged to arrive at a result. For example, results from a given polynomial curve formula and results from a given power curve formula can be averaged to provide a final predicted 5 minute reading.

It will be appreciated that the program for manipulating, interpreting or calculating results, using one or more types of regression analysis, will be internal to the particular reader, for example luminometer or photodiode based reader, or contained in a separate system to which the particular reader results are downloaded or otherwise accessible. It will also be appreciated that there are many derivations of the above specific equations and that the above equations are provided by way of example only.

Prediction of a 300 second, or other extended time counts, from a shorter time count, can also be made using a variable time assay. Such a variable time assay can be useful if RLU counts are increasing during, for example, the first 20 second count. If the counts are increasing more then predicted the RLU may be lower than what the actual might have been if the full, for example, 300 one second counts were taken. To reduce or eliminate this problem the RLU count can be summed over a time frame until the counts obtained do not vary significantly from the average of the accumulated sum. For example, the RLU count can be accumulated over 20 seconds and then a determination can be made by the software program whether or not the RLU count is significantly increasing from either the average summed RLU count or the RLU count at the 20th second. If, on the one hand, the additional RLU count, for example from the count at the 20th second, is less than a predefined percentage, for example 20%, of the average of the accumulated RLU counts, then the summed RLU count at 20 seconds is used to estimate the RLU count at 300 seconds. If, on the other hand, the RLU count at the 20th second is greater than a predefined percentage, for example, 20%, of the average of accumulated RLU counts at 20 seconds, then additional RLU counts are accumulated until the RLU count at any given second is less than the average of the summed RLU counts up to that time. The total RLU counts summed at that time are then used to estimate the extended count RLU, for example the projected 300 second count.

Another method for projecting longer time period RLU counts from shorter time period counts is using a lookup table. For example, if RLU counts are increasing during the first 20 seconds then the correction to predict the 300 second RLU count is greater than that used when the RLU count is decreasing toward the end of the 20 second count. For example, if the RLU count is 3000 at 20 seconds, and the curve is decreasing, then multiply the $20^{th}$ second count by 20. If the RLU count is 10000, and the curve is increasing, then the highest point on the RLU curve has not been reached. The $20^{th}$ second count would, therefore, be multiplied by a higher number, for example 50. Such a lookup table that can be included as part of a software program, can be used and adapted in a variety of ways. For example, if the reading is 3000 at the $20^{th}$ second multiply by 3, if 5000 then by 5, if 8000 then by 7. In another example a set equation is used.

Conversion of counts per second to counts per minute can be accomplished by multiplying each 1 second count by 60. In particular embodiments the luminometer, or other reader, is adjusted by reference to a standard. For example, adjusting luminometers by reference to a control luminometer standardizes readings from one luminometer to another for a given set of reagents and a given sample. Correction factors are used to make the adjustments. Examples of corrections factor amount are between about 200 and about 300. A formula used to calculate the correction factor can be:

cpm*10/correction factor, where cpm is counts per minute calculated from a counts per second reading. The correction factor is determined by results from a particular luminometer with reference to a control luminometer.

In addition to the various luciferin, luciferase, buffers, detergents and other reagents described herein, it is possible to use the methods and devices for counting and extrapolating described herein with other reagent systems, particularly those for measuring and detecting ATP. In various embodiments, reagents allowing regeneration of ATP, such as described by Foote et al, U.S. Pat. No. 6,043,047, issued Mar. 28, 2000 and regeneration of luciferin such as described by Kurosawa et al, EP 1 306 435 A1, published May 2, 2003, may be used.

It will be appreciated to those skilled in the art that the various herein described methods of reading and calculating a hygiene test result, such as using an extended or cumulative count alone or in conjunction with regression analysis, and thereby detecting surface residue contamination, are not limited to detection of ATP using luciferin-luciferase based luminescence detection. For example certain of these methods may be usefully applied to reading and analyzing the results from color based tests, for example color tests for detection of protein, glucose or other carbohydrates or phosphates such as those described in U.S. patent application Ser. No. 10/343,582 (Hygiene Monitoring), Jan. 31, 2003 which is incorporated herein by reference.

Other examples of tests for which the herein described method of reading and extrapolating (predicting) a hygiene test result may be used, which may not involve ATP detection or luminescence output, include those described in U.S. Pat. No. 6,551,834, Issued Apr. 22, 2003 (Detection of Contaminants Using Self-Contained Devices Employing Target Material Binding Dyes); U.S. Pat. No. 6,387,650, Issued May 14, 2002 (Method and Composition for Detecting Bacterial Contamination in Food Products); U.S. Pat. No. 6,043,047, issued Mar. 28, 2000 (Sample-Collecting and Assay Device For Use In the Detection of Biological Material) and European Patent 0 695 363 B1, Sep. 17, 1997 (Detection of Biological Material).

DESCRIPTION OF THE FIGURES

FIGS. 1A and 1B show the format of the POCKETSWAB-PLUS type device (the format of the POCKETSWAB Ultra/H2O Plus/ALLERGIENE test device is basically the same with only a change in the BAR solution as described herein). FIG. 1A is a schematic view of the swab removed form the test device and FIG. 1B is a schematic view of the test device containing the swab. In use of the swab type device, the swab 1 is removed from the body 3, by gripping the swab handle 2, and a 4"×4" surface, for example a food contact surface, is swabbed using the pre-moistened swab 1. (The swab 1 is provided pre-moistened, for example, with the same BAR solution provided in the niblet 5.) Alternatively the swab 1 can be dipped into the sample or the sample can be pipetted onto the swab 1. The swab 1 is then reinserted into the body 3 and screwed longitudinally through the covering 9 of the microtube test unit 4 and through the covering 10 of the niblet 5 and into bottom of the microtube test unit 4. In an embodiment, the liquid reagent niblet 5 contains, a BAR solution such as those described herein. The liquid within the BAR solution niblet 5 dissolves the reagent 7 containing luciferin-luciferase. The resulting luminescence is read using a luminometer. Alternatively the luciferin and luciferase reagents can be in the niblet 5 with the BAR solution in the bottom of the microtube test unit 4.

Figure 2:
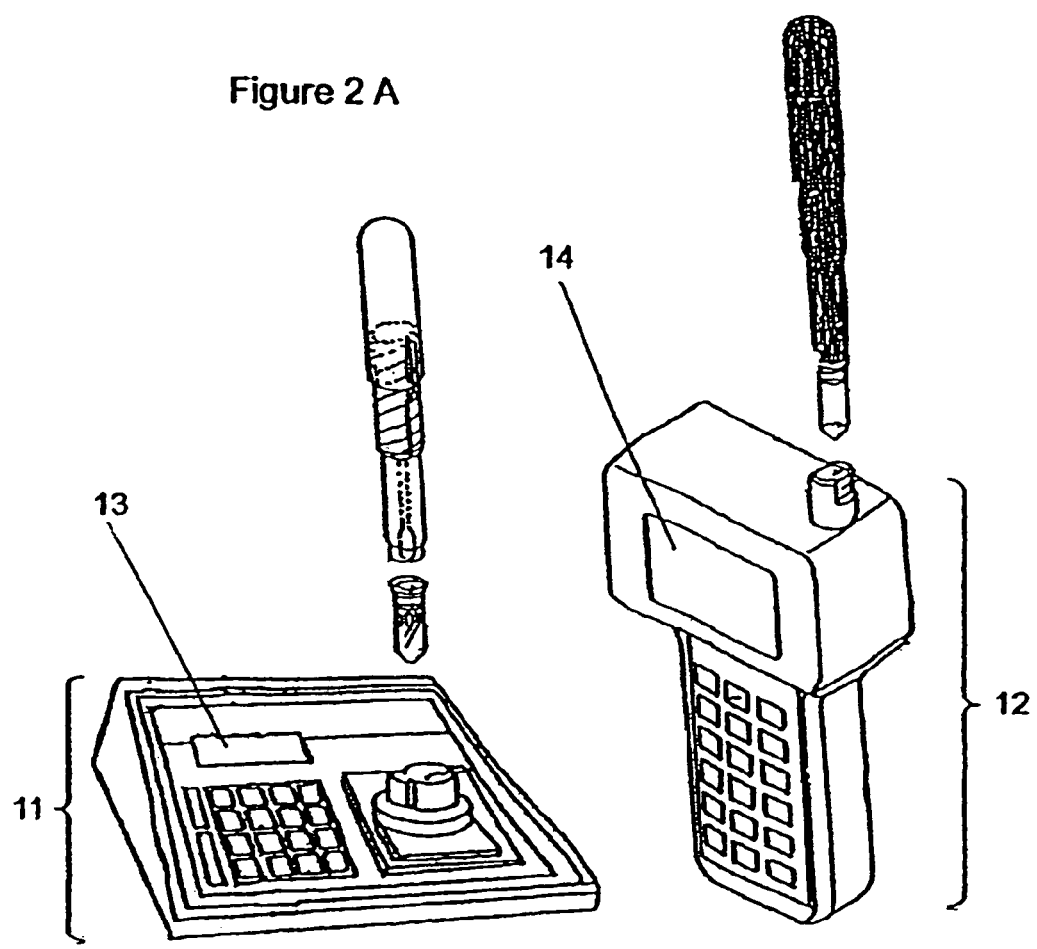
FIG. 2A shows insertion of a vial into a bench-top luminometer and FIG. 2B shows insertion of a complete test device into a hand-held luminometer.

FIGS. 2A and 2B illustrate insertion of the POCKETSWAB PLUS TEST device, or POCKETSWAB Ultra/H2O Plus/ALLERGIENE Test Device into a Charm LUMINATOR-K 11 and Charm LUMINATOR-T 12). Results are read using, for example, one of the methods described elsewhere herein, and a result is provided on the display 13, 14. The result can be provided, for example numerically or, alternatively, as a positive or negative.

Figure 3:
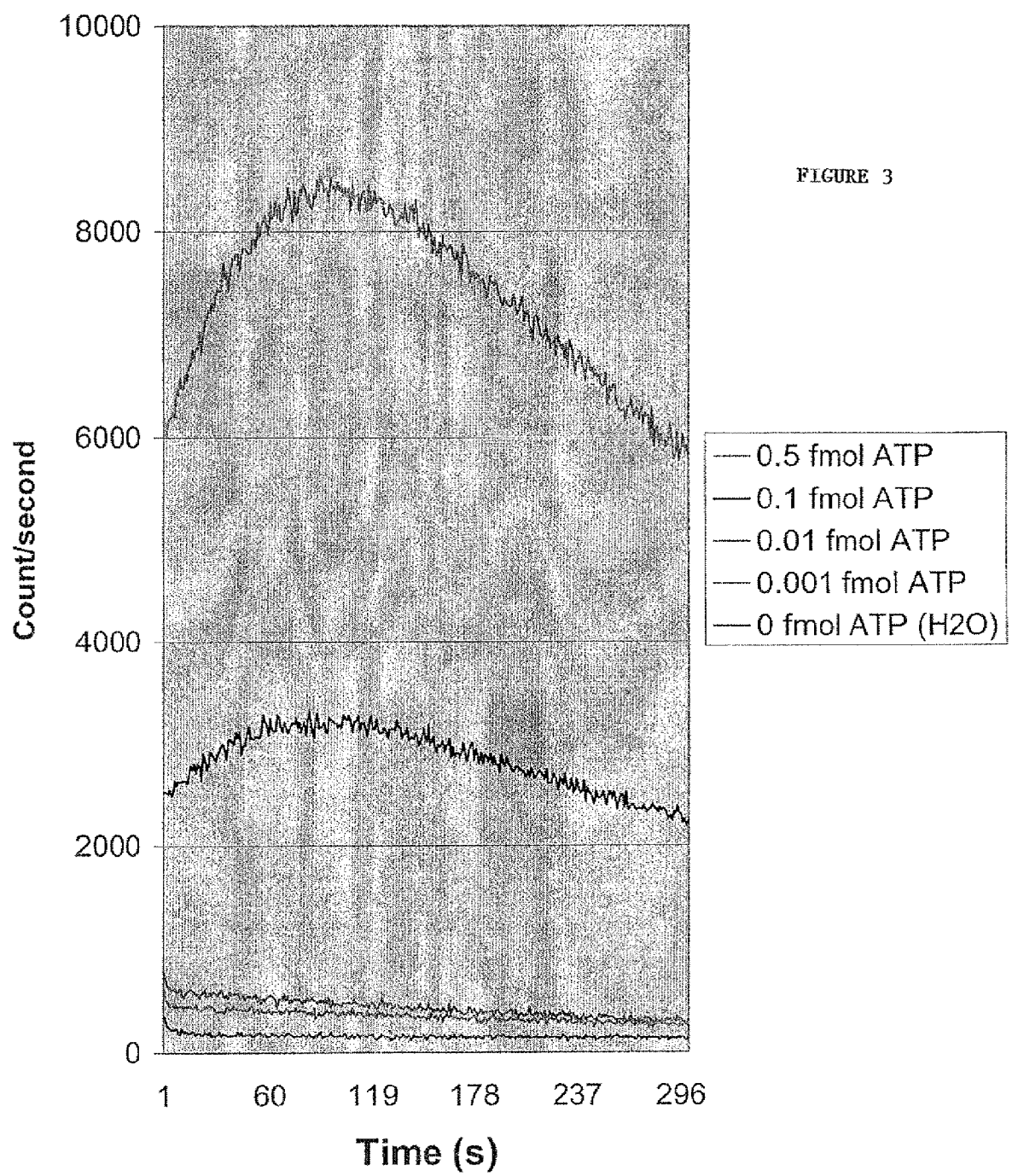
FIG. 3 graphically shows photon counters per second as a function of time at various ATP concentrations (0.5, 0.1, 0.01, 0.001 and 0 fmol ATP).

FIG. 3 is a graphical representation of data generated using various concentrations of ATP represented in the graph legend as femtomoles ATP. BAR solution contained 99.995% Butterfield's Buffer with 0.005% benzalkonium chloride. Light output was read using a LUMINATOR-T. Three hundred accumulated count per second/second readings (5 minutes total) were used to generate each line on the graph. This graph illustrates that a cumulative reading over an extended period of time, as opposed to an average or a reading of the amplitude (peak), allows the user to distinguish lower levels of ATP.

Figure 4:
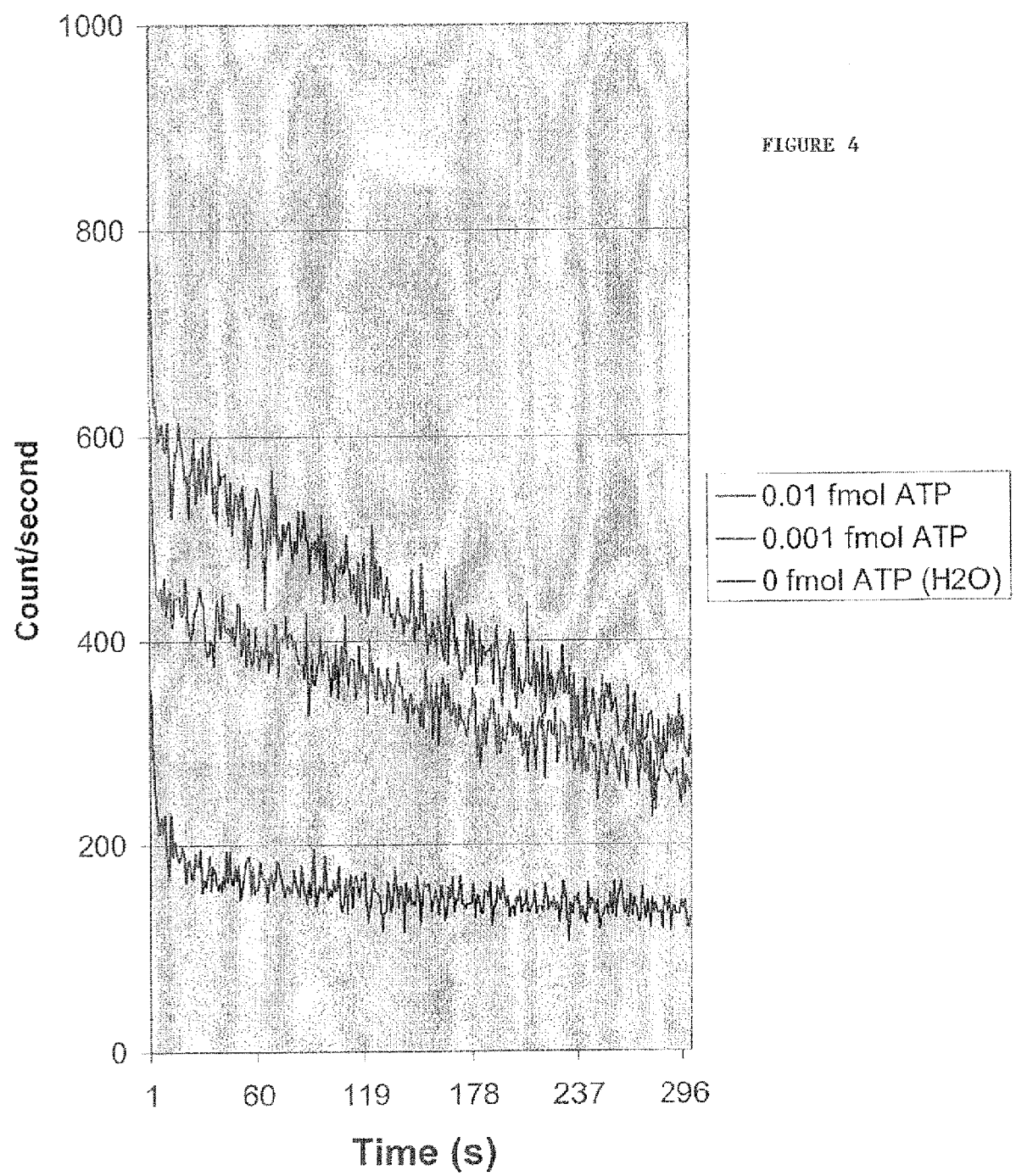
FIG. 4 graphically shows photon counters per second as a function of time at various low ATP concentrations (0.01, 0.001 and 0 fmol ATP).

FIG. 4 is a graphical representation of a subset of data from FIG. 3. The scale of the graph, from 0 to 1000 RLU's, further illustrates assay sensitivity relative to relatively low levels (0.01 fmol and 0.001 fmol) of ATP.

FIGS. 5A, 5B, 5C, and 5D are graphical representations of data generated by four different types of regression analysis:

power curve fit—FIG. 5A; linear trend fit—FIG. 5B; exponential curve fit—FIG. 5C; and polynomial curve fit—FIG. 5D.

The results shown in FIGS. 6 and 7 (power curve), 8 and 9 (exponential curve), 10 and 11 (linear trendline), 12 and 13 (polynomial curve), and 14 and 15 (average of exponential and power curves) were generated using two different LUMINATOR-T analyzers. Results were generated using five different concentrations of ATP (including zero). Correction factors were used to standardize results from both analyzers to within 5% of a control unit. The average of the corrected values was used. Average of multiple results for 20 second cumulative counts were compared to the average of multiple results from 300 second cumulative counts each for two separate LUMINATOR-T units. For each of FIGS. 6 through 15, column 1 (Col 1) shows the results of 20 cps (counts per second) counts summed at 20 seconds. For each of FIGS. 6 through 15, column 2 (Col 2) shows the results of the conversion of cps to counts per minute (cpm) by multiplying Col 1 times 60. For each of FIGS. 6 through 15, column 3 (Col 3) shows the corrected value which is calculated by multiplying by 10 the Col 2 results and dividing the product by the correction factor (CF) for the particular LUMINATOR-T used. For each of FIGS. 6 through 15, column 4 (Col 4) shows the actual relative light unit (RLU) results generated by summing 300 cps counts after 300 seconds.

The average results were subjected to various types of regression analysis to determine a best fit formula for each type of regression analysis. Column 5 (Col 5) in FIGS. 6 and 7 (Power Curve Analysis) used the regression formula $y=1.2539*x^{(1.183)}$, to use 20 second results to calculate 300 second results: $R=0.99914$. Column 5 (Col 5) in FIGS. 8 and 9 (Exponential Curve Analysis) used the regression formula $y=59597*e^{(3.3426E-05x)}$, to use 20 second results to calculate 300 second results: $R=0.99357$. Column 5 (Col 5) in FIGS. 10 and 11 (Linear Curve Analysis) used the regression formula $y=-60594+11.261x$, to use 20 second results to calculate 300 second results: $R=0.99805$. Column 5 (Col 5) in FIGS. 12 and 13 (Polynomial Curve Analysis) used the regression formula $y=-13737+7.5027*x+3.9039E-05x^2$: to use 20 second results to calculate 300 second results: $R=0.99909$. Column 5 (Col 5) in FIGS. 14 and 15 (Average of Exponential and Power Curves) used the regression formula $y=[(59597*e^{(3.3426E-05x)})+(1.2539*x^{(1.183)})]/2$ to use 20 second results to calculate 300 second results. The results show that one or more of the best fit formulas, alone or in combination, have R values sufficiently close to 1.0 to be able to accurately predict 5 minute cumulative results from actual 20 second cumulative results. Column 6 (Col 6) shows the percentage change of regression formula predicted results (Col 4) from actual 300 second results (Col 5).

It will be appreciated by those skilled in the art that 20 seconds and 5 minutes are representative time frames and are not provided as limitations on the scope of the invention.

Figure 16:
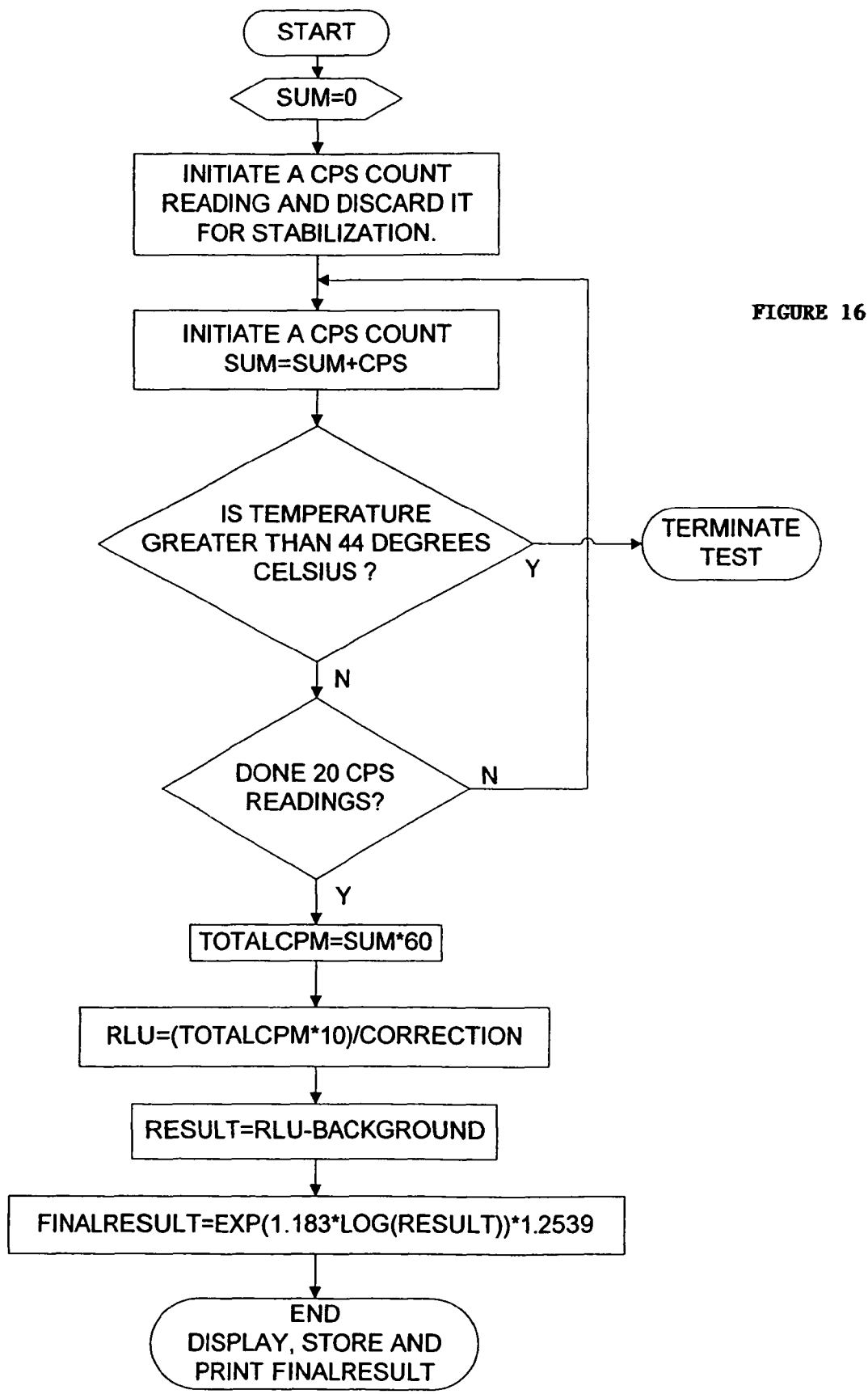
FIG. 16 is a flow chart showing an example of an accumulative algorithm to increase ATP sensitivity of a luminometer using a 20 second count to predict and extended count.

FIG. 16 is a flow chart showing an example of an accumulative algorithm to increase ATP sensitivity of the Charm Luminometer. The flow chart demonstrates obtaining a 20 second result and using that 20 second result to compute a final result (predicted 5 minute result). Terms used in the flow chart include:

1) Correction—a value determined by a calibration technician to slope the result to match a pre-calibrated standard Luminometer.
2) Background—a value determined by a calibration technician to set a threshold at which detection of a contaminant is obtained and begins to show a positive result.
3) RLU—Relative Light Units.
4) CPS—Counts Per Second.
5) Total CPM—total of CPS counts multiplied by 60 to predict Total Counts per minute.
6) Exp(x)—a Math library function which returns the exponential value of x.
7) nl(x)—a Math Library function which returns the natural logarithm of x (base $e=2.718282$).

The algorithm can be within a program internal to the luminometer or in an external component to which data is transferred, such as an associated central processing unit. The particular algorithm/flowchart shown in FIG. 16 provides a method for reading luminescent test results that includes a series of count per second readings. In this algorithm the initial count is discarded to avoid the possible impact of an initial aberrant result. An internal temperature check can be included to avoid incorrect results caused by excessive luminometer temperatures. Twenty separate CPS iterations are determined and summed. The total sum of the twenty CPS's can then be multiplied by 60 to arrive at a relative CPM value. The RLU result can be determined by multiplying the CPM value by a factor of 10 and dividing by Correction. The Correction having been determined by calibration to provide for consistent readings from instrument to instrument. That corrected number can then be reduced by the Background to arrive at the Result. That Result can then be used to extrapolate a predicted Final Result after an extended count, in this example using the power curve formula described.

Figure 17A:
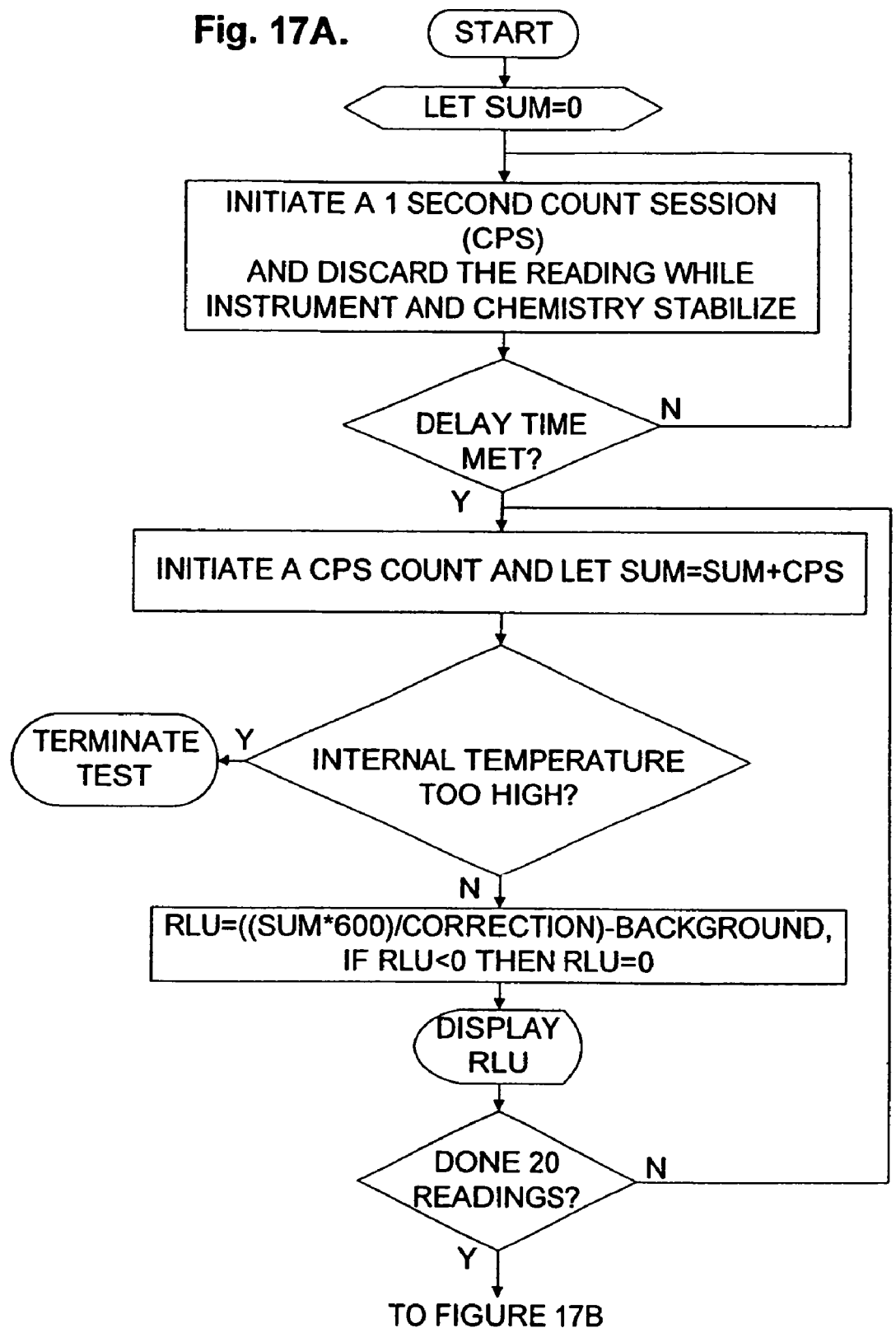
FIGS. 17A and 17B show a flow chart showing an example of an alternative accumulative algorithm to increase ATP sensitivity of a luminometer using a 20 second count to predict and extended count.
Figure 17B:
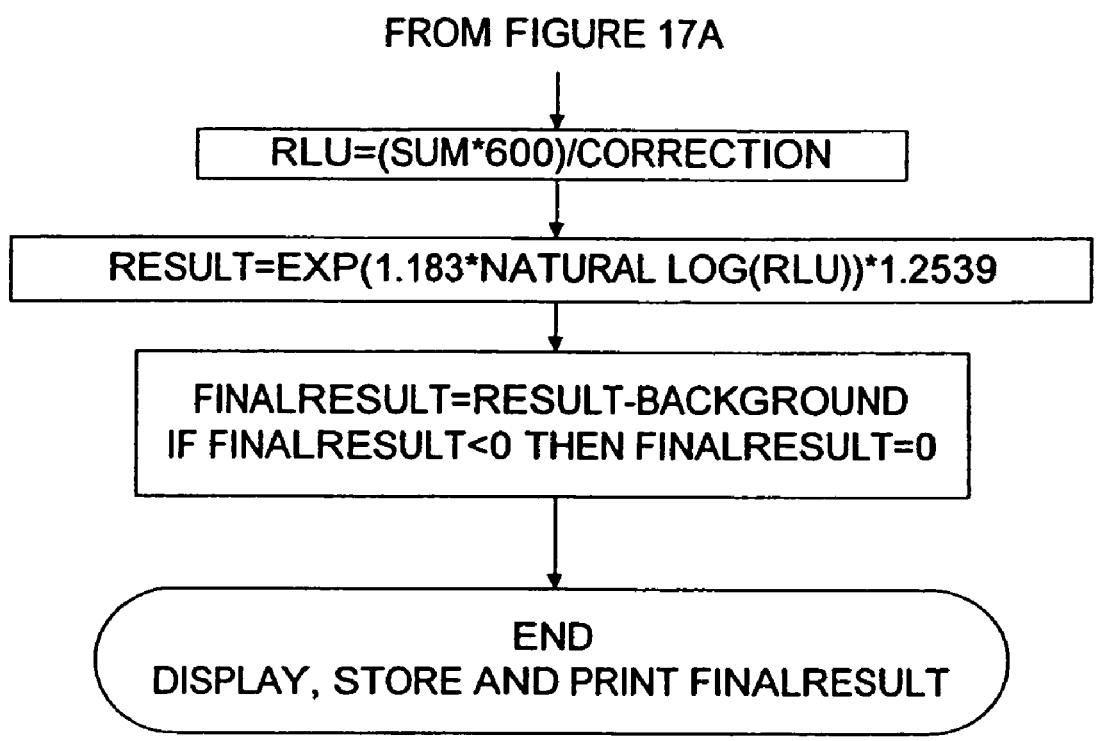

Another useful algorithm is shown in FIGS. 17A and 17B. In this algorithm the initial one second count is discarded to avoid the possible impact of an initial aberrant result. This step can be repeated multiple times, for a pre-determined Delay Time, to allow additional reagent and instrument stabilization, if necessary. In this algorithm a visual indication of result is provided after each RLU calculation so that the user can observe results after each count summation and calculation and, therefore, terminate the test earlier if a positive result is established. The total sum of the twenty CPS's can then be multiplied by 600 and divided by the Correction to simplify the equation. In this example, as distinguished from the example provided in FIG. 16, Background counts are deducted from the Final Result after the extended count prediction formula is applied.

EXAMPLES

Example 1

BAR solution containing 99.995% modified Butterfield's Buffer (made with dibasic rather than monobasic phosphate) with 0.005% benzalkonium chloride was prepared as follows:

A. Prepare 1 L of 0.195 M dibasic potassium phosphate as follows:
  1. Add 34 g dibasic potassium phosphate ($K_2HPO_4$; FW=174.2) to 500 mL ultra-pure water in a 1 liter Erlenmeyer flask. Mix until fully dissolved.
  2. Adjust pH to 7.20±0.02 with phosphoric acid.
  3. Bring volume to 1 L with ultra-pure water. Mix for 5 minutes.
B. Prepare 22 L of BAR solution (0.24 mM dibasic potassium phosphate) as follows:
  1. Add 27.5 mL of 0.195 M dibasic potassium phosphate to carboy with mark at 22 L.
  2. Bring volume to 22 L with ultra-pure water. Mix for 5 minutes.

3. Dispense 3500 mL of BAR solution into six×4 L NAL-GENE (Nalgene is a registered trademark of Nalge Nunce International Corporation Rochester, N.Y.)

C. Autoclave the bottles of BAR solution for 90 minutes at 121° C.

D. After autoclaving add 350 μL of 50% benzalkonium chloride to each bottle of BAR solution once the solution has cooled to room temperature. Shake well for 30 seconds to mix.

The above described BAR solution can be used with luciferin-luciferase reagents to detect ATP. In one example luciferin-luciferase were produced using highly purified beetle D-Luciferin free acid from Regis Technologies, Inc., Catalog #360100; and r-luciferase was from PROMEGA, specific activity $3.3 \times 10^{10}$ relative light units per mg protein (minimum specification $2.0 \times 10^{10}$ relative light units per mg protein). The luciferin and luciferase were freeze dried together with magnesium acetate and ATP-free bulking and stabilizing agents such as lactose, BSA, glycine (1.4 millimolar glycine when combined with 300 microliter BAR solution), ethylenediaminetetraacetic Acid (EDTA), dithiothreitol (DTT), and stabilizers such as lactose, and tableted after addition of AVICEL and magnesium stearate. The ratio of luciferin to BAR solution was about 0.073 micrograms luciferin per microliter BAR solution. The ratio of luciferase to BAR solution ratio was about 0.0073 micrograms luciferase per microliter buffer.

Example 2

For testing, 300 μL of BAR solution was used (various compositions described below) and either luciferin-luciferase liquid solution, with magnesium co-factor or without magnesium cofactor. Tableted luciferin-luciferase (which contains additional stabilizers and magnesium cofactor) was also tested for comparison. In either case, the amount of luciferin per test was 23 μg, and the amount of luciferase was 2.3 μg. Luciferin/Luciferase tablet includes co-factor, stabilizers and bulking agents including: magnesium acetate, lactose, BSA, glycine, EDTA, DTT, lactose, AVICEL (AVICEL is a registered trademark of FMC Corporation, Philadelphia, Pa.) and magnesium stearate. Luciferin/Luciferase liquid includes only luciferin and luciferase or alternatively as indicated luciferin and luciferase and magnesium. LUM-T background was set to 100 ("off") in order to see differences in uncorrected background values. Results presented in Table 1 show that of the various niblet solutions tested those with Butterfield's Buffer and 0.005% benzalkonium chloride had the best positive to negative ratio. The niblet solution including 260 mM Tris base/75 mM tricine, pH 7.8 is used in the niblet solution for the "standard" POCKETSWAB PLUS (Charm Sciences, Inc. Lawrence, Mass.). These results show maximum sensitivity using a BAR solution of BB+BC as compared with other possible BAR solutions. In table 1 the abbreviation BB stands for Butterfield's Buffer prepared with dibasic potassium phosphate and the abbreviation BC stands for benzalkonium chloride.

TABLE 1

| Niblet Solution Composition | Luciferin-Luciferase | Negative RLU Avg | 0.01 fmol ATP RLU Avg | Pos/Neg Ratio |
|---|---|---|---|---|
| Control (BB 99.995% + BC 0.005%) | tablet | 55746 | 190453 | 3.42 |
| Sterile water | tablet | 57571 | 98742 | 1.72 |
| BB alone (no BC) | tablet | 47199 | 142736 | 3.02 |
| 260 mM Tris base/75 mM Tricine; pH 7.8 | tablet | 48869 | 66665 | 1.36 |
| 20 mM Tris base/ 5 mM Tricine; pH 7.8 | tablet | 75869 | 151421 | 2.00 |
| Control (BB 99.995% + BC 0.005%) | liquid | 37596 | 40595 | 1.08 |
| Sterile water | liquid | 33300 | 32186 | 0.97 |
| Control (BB 99.995% + BC 0.005%) | Liquid + Mg | 53230 | 169660 | 3.19 |

Example 3

An embodiment involves detection of bacterial contamination in water, for example food production water, rinse water or wet surfaces from cleaned equipment. In this embodiment a sample swab is dipped in sample water and swirled for approximately 5 seconds. After removal from the water sample, the swab is contacted with BAR solution, for example BAR solution containing 99.995% dibasic phosphate buffer and 0.005% benzalkonium chloride. The phosphate buffer has molarity in the range of about 0.1 millimolar to about 0.5 millimolar. After adding sample to the BAR solution the mixture is contacted with the luciferin/luciferase reagents for example the tablet described with reference to Example 1. Luminescence results are determined on a standard luminometer, for example a LUMINATOR-T, FIREFLY, LUMGIENE or NOVALUM (Charm Sciences, Inc.), utilizing a 20 second cumulative count and Power Curve generated result.

Examples 4-7

NOTE: The following examples 4-7 and related tables show detection levels for common food residues, for example 5 ppm peanut butter. Generally, the allergenic component of the food, such as peanut butter, is a protein. As a result, detection levels may refer to peanut butter protein levels rather than peanut butter levels. If peanut butter is detected at 5 ppm and peanut butter is, generally, about 22% protein then peanut butter protein can be detectable at 5 ppm×0.22, or approximately 1.1 ppm protein.

Example 4

Table 2 shows results using a BAR solution of 99.995% dibasic phosphate buffer and 0.005% benzalkonium chloride to test various potentially allergenic matrices (unsalted cocktail peanuts, peanut butter, pasteurized whole milk, raw egg white, raw whole egg, all-purpose flour) at a variety of concentrations. A 5000 ppm stock solution of each food was prepared in sterile water, then diluted serially in sterile water. Results were generated on a luminometer utilizing a 30 second cumulative RLU count and a background subtract of 15000. For testing, a 20 microliter sample was added directly to a swab. A LUMINATOR-K was used.

Luciferin-luciferase was as described in Example 1. The results show ATP detection at levels at which a positive result can be used to determine, for example, that peanut butter may be present at above 5 ppm.

TABLE 2

| Allergen/Source | | RLU Cumulative | % Positive |
|---|---|---|---|
| Blank (negative control) | | 0 | 0% |
| Unsalted cocktail peanuts (25% protein) | Peanut | | |
| | 5000 ppm | 711557 | 100% |
| | 500 ppm | 65217 | 100% |
| | 50 ppm | 8247 | 100% |
| | 25 ppm | 6630 | 100% |
| | 5 ppm | 0 | 0% |
| Peanut butter (22% protein) | Peanut Butter | | |
| | 5000 ppm | 957200 | 100% |
| | 500 ppm | 101881 | 100% |
| | 50 ppm | 7851 | 100% |
| | 25 ppm | 7072 | 100% |
| | 5 ppm | 1850 | 33% |
| Pasteurized whole milk (~2.7% casein) | Milk | | |
| | 18500 ppm | 2447813 | 100% |
| | 1850 ppm | 284021 | 100% |
| | 185 ppm | 19942 | 100% |
| | 37 ppm | 1773 | 50% |
| Raw egg white (~10% protein) | Egg White | | |
| | 50000 ppm | 20263 | 100% |
| | 25000 ppm | 11270 | 100% |
| | 10000 ppm | 768 | 100% |
| | 5000 ppm | 2519 | 50% |
| Raw whole egg (~6.7% egg white protein) | 5000 ppm | 72812 | 100% |
| | 500 ppm | 16578 | 100% |
| | 250 ppm | 4939 | 100% |
| | 50 ppm | 0 | 0% |
| All-purpose flour (~10% protein) | Flour | | |
| | 5000 ppm | 266208 | 100% |
| | 500 ppm | 34620 | 100% |
| | 250 ppm | 34188 | 100% |
| | 100 ppm | 1780 | 100% |
| | 50 ppm | 0 | 0% |

Example 5

Table 3 shows results using a BAR solution of 99.995% dibasic phosphate buffer and 0.005% benzalkonium chloride with luciferin/luciferase described in Example 1, to test the same allergenic matrices as Example 4. A 5000 ppm stock solution of each food was prepared in sterile water, then diluted serially in sterile water. A 5 second average RLU (non-cumulative in which five RLU counts per second over five seconds are averaged) count and a background subtract of 2600 were used. For testing, a 20 microliter sample was added directly to a swab. A LUMINATOR-K was used. Sensitivity decreased as compared to results shown in Example 4.

TABLE 3

| Allergen | Source | RLU | % Positive |
|---|---|---|---|
| Blank (negative control) | | 0 | 0% |
| Unsalted cocktail peanuts (25% protein) | Peanut | | |
| | 5000 ppm | 16575 | 100% |
| | 500 ppm | 679 | 50% |
| | 50 ppm | 0 | 0% |
| | 25 ppm | 0 | 0% |
| | 5 ppm | 0 | 0% |
| Peanut butter (22% protein) | Peanut Butter | | |
| | 5000 ppm | 22264 | 100% |
| | 500 ppm | 1000 | 50% |
| | 50 ppm | 0 | 0% |
| | 25 ppm | 0 | 0% |
| | 5 ppm | 0 | 0% |
| Pasteurized whole milk (~2.7% casein) | Milk | | |
| | 18500 ppm | 62521 | 100% |
| | 1850 ppm | 5687 | 100% |
| | 185 ppm | 0 | 0% |
| | 37 ppm | 0 | 0% |
| Raw egg white (~10% protein) | Egg White | | |
| | 50000 ppm | 0 | 0% |
| | 25000 ppm | 0 | 0% |
| | 10000 ppm | 0 | 0% |
| | 5000 ppm | 0 | 0% |
| Raw whole egg (~6.7% egg white protein) | Whole Egg | | |
| | 5000 ppm | 0 | 0% |
| | 500 ppm | 0 | 0% |
| | 250 ppm | 0 | 0% |
| | 50 ppm | 0 | 0% |
| All-purpose flour (~10% protein) | Flour | | |
| | 5000 ppm | 4663 | 100% |
| | 500 ppm | 0 | 0% |
| | 250 ppm | 0 | 0% |
| | 100 ppm | 0 | 0% |
| | 50 ppm | 0 | 0% |

Example 6

Table 4 shows results using BAR solution of 260 mM Tris base/75 mM tricine, pH 7.8 (as previously used in the POCK-ETSWAB-PLUS test). Luciferin-luciferase described in Example 1. The same allergenic matrices were tested as in Example 4. A 5000 ppm stock solution of each food was prepared in sterile water, then diluted serially in sterile water. Results were generated on a luminometer utilizing a 5 second average RLU (non-cumulative in which five RLU counts per second over five seconds are averaged) count and a background subtract of 2600. For testing, a 20 microliter sample was added directly to a swab. A LUMINATOR-K was used. Results show decreased sensitivity as compared with results in both Example 4 and Example 5.

TABLE 4

| Allergen | Source | RLU | % Positive |
|---|---|---|---|
| Blank (negative control) | | 0 | 0% |
| Unsalted cocktail peanuts (25% protein) | Peanut | | |
| | 5000 ppm | 1916 | 100% |
| | 500 ppm | 0 | 0% |
| | 50 ppm | 0 | 0% |
| | 25 ppm | 0 | 0% |
| | 5 ppm | 0 | 0% |
| Peanut butter (22% protein) | Peanut Butter | | |
| | 5000 ppm | 4399 | 100% |
| | 500 ppm | 0 | 0% |
| | 50 ppm | 0 | 0% |
| | 25 ppm | 0 | 0% |
| | 5 ppm | 0 | 0% |
| Pasteurized whole milk (~2.7% casein) | Milk | | |
| | 18500 ppm | 18473 | 100% |
| | 1850 ppm | 2276 | 100% |
| | 185 ppm | 0 | 0% |
| | 37 ppm | 0 | 0% |
| Raw egg white (~10% protein) | Egg White | | |
| | 50000 ppm | 0 | 0% |
| | 25000 ppm | 0 | 0% |
| | 10000 ppm | 0 | 0% |
| | 5000 ppm | 0 | 0% |
| Raw whole egg (~6.7% egg white protein) | Whole Egg | | |
| | 5000 ppm | 0 | 0% |
| | 500 ppm | 0 | 0% |
| | 250 ppm | 0 | 0% |
| | 50 ppm | 0 | 0% |
| All-purpose flour (~10% protein) | Flour | | |
| | 5000 ppm | 0 | 0% |
| | 500 ppm | 0 | 0% |
| | 250 ppm | 0 | 0% |

TABLE 4-continued

| Allergen | Source | RLU | % Positive |
|---|---|---|---|
| | 100 ppm | 0 | 0% |
| | 50 ppm | 0 | 0% |

Example 7

Table 5 shows results using a BAR solution of 99.995% dibasic phosphate buffer and 0.005% benzalkonium chloride with luciferin/luciferase described in Example 1, to test various concentrations of potentially allergenic matrices. A 5000 ppm stock solution of each food was prepared in sterile water, then diluted serially in sterile water. A 5 minute cumulative count was used. Background subtract of 100,000 was used. A LUMINATOR-K was used. Increased sensitivity, as compared with results from the next most sensitive combination (results in Example 4) was observed.

Further experiments, using a 10 minute cumulative count, increased sensitivity to egg white to 5 ppm (approximate egg white protein equivalent of 0.5 ppm). It is expected that sensitivity to other matrices may also be increased using such an extended cumulative count.

TABLE 5

| Food | Concentration | RLU Average | % Positive | Allergen Test Manufacturer Claims |
|---|---|---|---|---|
| Peanut butter (22% protein) | 5 ppm | 747242 | 100% | <0.1 to 1 ppm |
| | 0.5 ppm | 83137 | 100% | peanut protein |
| | 0.25 ppm | 60753 | 100% | (0.5 to 3 hr assay time) |
| | 0.1 ppm | 59232 | 67% | |
| | 0.05 ppm | 5188 | 33% | |
| Soy nuts (36.7% protein) | 50 ppm | 199083 | 100% | 70 to <5000 ppm |
| | 5 ppm | 61132 | 100% | soy protein |
| | 0.5 ppm | 9414 | 100% | (30 min assay time) |
| | 0.05 ppm | 0 | 0% | |
| Almond (20% protein) | 50 ppm | 217604 | 100% | 1.7 to 5 ppm |
| | 5 ppm | 71092 | 100% | almond |
| | 0.5 ppm | 4396 | 50% | (30 min assay time) |
| Walnut (16.7% protein) | 50 ppm | 182168 | 100% | unknown |
| | 5 ppm | 51090 | 100% | |
| | 0.5 ppm | 225 | 50% | |
| Pecan (10% protein) | 50 ppm | 76873 | 100% | unknown |
| | 5 ppm | 10257 | 100% | |
| | 0.5 ppm | 0 | 0% | |
| Egg white (10% protein) | 5000 ppm | 224516 | 100% | 1 to 5 ppm egg |
| | 500 ppm | 40575 | 100% | white protein |
| | 100 ppm | 33374 | 100% | (0.5 to 1.5 hr assay time) |
| | 50 ppm | 7860 | 67% | |
| Whole egg (6.7% protein) | 500 ppm | 41404 | 100% | 1 to 5 ppm egg |
| | 50 ppm | 40977 | 100% | white protein |
| | 5 ppm | 6809 | 67% | (0.5 to 1.5 hr assay time) |
| | 0.5 ppm | 187 | 33% | |
| Whole milk, pasteurized (2.7% casein) | 100 ppm | 223233 | 100% | 5 ppm |
| | 10 ppm | 105121 | 100% | milk protein |
| | 1 ppm | 29771 | 67% | (0.5 to 2 hr assay time) |
| Whole wheat four (13.3% protein) | 100 ppm | 440020 | 100% | <2 to 8 ppm |
| | 10 ppm | 77042 | 100% | wheat proteins |
| | 1 ppm | 26010 | 100% | (0.5 to 2 hr assay time) |
| | 0.1 ppm | 32217 | 67% | |
| All-purpose white four (10% protein) | 10 ppm | 82308 | 100% | <2 to 8 ppm |
| | 1 ppm | 29483 | 100% | wheat proteins |
| | 0.1 ppm | 0 | 0% | (0.5 to 2 hr assay time) |
| Clams, raw (12.8% protein) | 50 ppm | 130018 | 100% | unknown |
| | 25 ppm | 55383 | 100% | |
| | 10 ppm | 28197 | 40% | |
| | 5 ppm | 0 | 0% | |
| Shrimp, raw (20.3% protein) | 50 ppm | 129186 | 100% | unknown |
| | 25 ppm | 82211 | 100% | |
| | 10 ppm | 39574 | 80% | |
| | 5 ppm | 1613 | 33% | |
| Atlantic salmon, raw (19.9% protein) | 50 ppm | 48824 | 100% | unknown |
| | 25 ppm | 45425 | 100% | |
| | 10 ppm | 8237 | 60% | |
| | 5 ppm | 0 | 0% | |
| Soybeans (36.5% protein) | 50 ppm | 346842 | 100% | 70 to <5000 ppm |
| | 5 ppm | 30648 | 100% | soy protein |
| | 0.5 ppm | 3878 | 50% | (30 min assay time) |
| Sunflower seeds (20% protein) | 5 ppm | 93950 | 100% | unknown |
| | 0.5 ppm | 42704 | 100% | |
| | 0.05 ppm | 33843 | 40% | |
| Sesame seeds (17.7% protein) | 500 ppm | 508324 | 100% | 1 ppm sesame |
| | 50 ppm | 38680 | 100% | seed protein |
| | 25 ppm | 8551 | 60% | (assay time unknown) |
| Whole milk, powdered (19.7% casein) | 50 ppm | 399603 | 100% | 5 ppm |
| | 5 ppm | 50471 | 100% | milk protein |
| | 0.5 ppm | 16748 | 40% | (0.5 to 2 hr assay time) |

TABLE 5-continued

| Food | Concentration | | RLU Average | % Positive | Allergen Test Manufacturer Claims |
|---|---|---|---|---|---|
| Soy flour (52% protein) | 50 | ppm | 399366 | 100% | 70 to <5000 ppm |
| | 5 | ppm | 95755 | 100% | soy protein |
| | 0.5 | ppm | 31848 | 60% | (30 min assay time) |
| Whole milk, UHT (2.7% casein)* | 1000 | ppm | 32680 | 100% | 5 ppm |
| | 500 | ppm | 30557 | 100% | milk protein |
| | 250 | ppm | 10541 | 50% | (0.5 to 2 hr assay time) |
| | 100 | ppm | 2354 | 20% | |

Example 8

Tables 6, 7, 8, and 9 show results using using a BAR solution of 99.995% dibasic phosphate buffer and 0.005% benzalkonium chloride with luciferin/luciferase described in Example 1, to test various concentrations of ATP (Table 6) Whole Egg (Table 7), Peanut Butter (Table 8) and Egg White (Table 9). RLU counts were read every second for 300 seconds and totaled. Background subtract of 100,000 was used. Results in tables 6, 7, 8 and 9 show multiple RLU readings which were averaged to arrive at particular results. These results are also summarized in particular examples in Example 7 (Table 5). A LUMINATOR-K was used to detect the luminescence.

TABLE 6

| ATP Concentration (fmol/20 uL sample) | RLU Readings | % Positive |
|---|---|---|
| 0.5 | 4196324 | 100% |
| | 6406563 | |
| | 5501847 | |
| | Avg: 5368245 | |
| 0.1 | 4408690 | 100% |
| | 2138919 | |
| | 2345606 | |
| | Avg: 2964405 | |
| 0.01 | 213632 | 100% |
| | 250782 | |
| | 195101 | |
| | Avg: 219838 | |
| 0.001 | 99087 | 100% |
| | 37798 | |
| | 40974 | |
| | Avg: 59286 | |
| 0% | 0 | 0% |
| | 0 | |
| | 0 | |
| | Avg: 0 | |

TABLE 7

| Whole Egg Concentration (ppm) | RLU Readings | % Positive |
|---|---|---|
| 500 | 31407 | 100% |
| | 11446 | |
| | 81360 | |
| | Avg: 41404 | |
| 50 | 2715 | 100% |
| | 100510 | |
| | 19707 | |
| | Avg: 40977 | |
| 5 | 18516 | 67% |
| | 1911 | |
| | 0 | |
| | Avg: 6809 | |
| 0.5 | 562 | 33% |
| | 0 | |
| | 0 | |
| | Avg: 187 | |

TABLE 7-continued

| Whole Egg Concentration (ppm) | RLU Readings | % Positive |
|---|---|---|
| 0 | 0 | 0% |
| | 0 | |
| | 0 | |
| | Avg: 0 | |

TABLE 8

| Peanut Butter Concentration (ppm) | RLU Readings | % Positive |
|---|---|---|
| 5 | 889650 | 100% |
| | 628410 | |
| | 723666 | |
| | Avg: 747242 | |
| 0.5 | 135814 | 100% |
| | 54646 | |
| | 58950 | |
| | Avg: 83137 | |
| 0.25 | 3473 | 100% |
| | 42586 | |
| | 136200 | |
| | Avg: 60753 | |
| 0.1 | 116374 | 67% |
| | 61321 | |
| | 0 | |
| | Avg: 59232 | |
| 0.05 | 0 | 33% |
| | 0 | |
| | 15564 | |
| | Avg: 5188 | |
| 0 | 0 | 0% |
| | 0 | |
| | 0 | |
| | Avg: 0 | |

TABLE 9

| Egg White Concentration (ppm) | RLU Readings | % Positive |
|---|---|---|
| 5000 (500 ppm protein) | 147025 | 100% |
| | 302007 | |
| | Avg: 224516 | |
| 500 (50 ppm protein) | 47696 | 100% |
| | 35638 | |
| | 38391 | |
| | Avg: 40575 | |
| 100 (10 ppm protein) | 29355 | 67% |
| | 15956 | |
| | 54812 | |
| | Avg: 33374 | |
| 50 (5 ppm protein) | 12769 | 67% |
| | 0 | |
| | 10810 | |
| | Avg: 7860 | |
| 0 | 0 | 0% |
| | 0 | |
| | 0 | |
| | Avg: 0 | |

Example 9

Tables 10-13 show a comparison of RLU results using three different BAR solutions (referred to as BAR A, BAR B and BAR C). Luciferin/luciferase was described in Example 1. BAR A solution (original formulation from PocketSwab Plus swabs) contained 3.138% Trizma Base, 3.125% phosphoric acid detergent, 1.344% Tricine, 1.344% Triton X-100 (10% solution) and 0.172% benzalkonium chloride (10% solution) and deionized water. Displacement measurements for Trizma base and tricine were used to calculate the volume of deionized water needed. BAR B solution contained Butterfield's Buffer made with dibasic phosphate (less than about 1 millimolar). BAR C solution contained 99.995% Butterfield's Buffer made with dibasic phosphate (less than about 1 millimolar) with 0.005% benzalkonium chloride.

Table 10 shows the average RLU results from a comparison of BAR A, BAR B and BAR C using the luciferin/luciferase described with reference to Example 1 and Example 1 and varying concentrations of ATP from 0 to 180 femtomoles. Both the LUMT and FIREFLY luminometers were used with background subtract. Results show increased sensitivity by decreasing the molarity of the BAR solution, using only Butterfield's Buffer (low molarity phosphate buffer) made with dibasic phosphate. BAR C shows the best sensitivity when 0.005% benzalkonium chloride is added to Butterfield's Buffer made with dibasic phosphate.

TABLE 10

|       | LUMT    | FIREFLY |              |
|-------|---------|---------|--------------|
| BAR-A | 81,900  | 21,013  | 180 fmoles ATP |
| BAR-B | 129,933 | 34,459  |              |
| BAR-C | 218,366 | 65,112  |              |
| BAR-A | 8,368   | 752     | 18 fmoles ATP |
| BAR-B | 9,748   | 1,066   |              |
| BAR-C | 16,636  | 2,665   |              |
| BAR-A | 0       | 0       | 1.8 fmoles ATP |
| BAR-B | 0       | 0       |              |
| BAR-C | 2,869   | 0       |              |
| BAR-A | 0       | 0       | 0 fmoles ATP |
| BAR-B | 0       | 0       |              |
| BAR-C | 0       | 0       |              |

Table 11 shows comparative RLU results using BAR A, BAR B and BAR C and sample uptake by swabbing a surface contaminated with a variety of food residues. The results again show overall increased sensitivity using BAR C. Surface squares tested with finished unit on LUMINATOR-T with background subtract.

TABLE 11

| Solution | Chicken | Juice | Egg   | Milk  |
|----------|---------|-------|-------|-------|
| BAR-A    | 130582  | 3800  | 9902  | 4777  |
| BAR-C    | 169327  | 89186 | 60948 | 51338 |
| BAR-B    | 209985  | 24938 | 23509 | 29156 |

Table 12 shows the average RLU results from a comparison of BAR A, BAR B and BAR C using the luciferin/luciferase described in Example 1 and varying concentrations (dilutions) of a variety of bacteria by pipetting 10 microliters onto each swab. LUMINATOR-T was used with background subtract.

TABLE 12

Bacterial study done by pipetting 10 ul onto each swab system

| Solution | C. freundii | S. cerevisiae | P. agglomerans | P. fluorescens |       |
|----------|-------------|---------------|----------------|----------------|-------|
| BAR-A    | 10315       | 36163         | 30633          | 5931           | Diln  |
| BAR-C    | 15280       | 582814        | 45942          | 5525           | 10-2  |
| BAR-B    | 12603       | 56975         | 18555          | 21306          |       |
| BAR-A    | 0           | 2509          | 5180           | 0              | Diln  |
| BAR-C    | 115         | 53092         | 1953           | 513            | 10-3  |
| BAR-B    | 0           | 3828          | 14375          | 0              |       |
| BAR-A    | 0           | 0             | 8646           | 0              | Diln  |
| BAR-C    | 0           | 1556          | 275            | 0              | 10-4  |
| BAR-B    | 0           | 3868          | 3880           | 0              |       |

Tables 13A, 13B, 13C, 13D, 13E, 13F show results from a variety of stability, sensitivity and test background experiments.

Table 13A—The results show increased count stability between 1 and 2 minutes after test initiation using a 180 femtomole concentration of ATP and BAR A versus BAR C. Results shown are from the same test recounted and show that BAR C, in addition to increased sensitivity, provided increased test result stability. LUMINATOR-T with background subtract.

| | 180 fmoles | | | | |
|---|---|---|---|---|---|
|       | Initial  | 1 min    | % change | 2 min   | % change |
| BAR-A | 111,065  | 94,115   | −15%     | 70,426  | −37%     |
| BAR-C | 205,833  | 205,638  | −0.10%   | 196,642 | −4%      |

Table 13B—The results show a comparison of results using BAR B and BAR C testing a 60 femtomole concentration of ATP. LUMINATOR-K was used with no background subtract.

|       | Zero | 60 fmoles ATP |
|-------|------|---------------|
| BAR-B | 450  | 136,000       |
| BAR-C | 650  | 242,700       |

Table 13C—The results show count stability between an initial count and a one minute count, comparing BAR A and BAR C. LUMINATOR-T used with background subtract.

| 60 fmoles ATP | Initial Count | Count after 1 min. |
|---------------|---------------|--------------------|
| BAR-A         | 30,581        | 17,049             |
| BAR-C         | 252,365       | 240,069            |

Table 13D—The results show count stability between an initial count and a one minute count, comparing BAR A and BAR C in testing a 10 microliter sample of raw milk pipetted onto a swab and then the swab is contacted with the BAR solution. LUMINATOR-T used with background subtract.

|  | Initial count | Count after 1 min. |
| --- | --- | --- |
| BAR-A | 115,459 | 223,941 |
| BAR-C | 501,329 | 720,153 |

Table 13E—The results show temperature stability of BAR C in temperature stressed conditions versus standard conditions. LUMINATOR-K used with no background subtract.

|  | 0 count | 3.6 fmoles ATP |
| --- | --- | --- |
| BAR-C | 661 | 14,644 |
| BAR-C (stressed) | 711 | 15,173 |

Table 13F—The results show increased sensitivity to 1.8 femtomoles ATP using BAR C as compared to BAR B and BAR A. LUMINATOR-T used with background subtract.

|  | Zero check | 1.8 fmoles ATP |
| --- | --- | --- |
| BAR-A | 0, 0, 0, 0, 0 | 0, 0 |
| BAR-C | 0, 0, 0, 0, 0 | 3928/3236 |
| BAR-B | 0, 0, 0, 0, 0 | 828/567 |

TABLE 14

| Buffer | Zero | 0.05 fmol ATP | 0.01 fmol ATP |
| --- | --- | --- | --- |
| Control | 53248 | 269829 (5.1) | 149186 (2.8) |
| 250 mM | 24659 | 40448 (1.6) | 31084 (1.3) |
| 100 mM | 31808 | 160852 (5.1) | 63116 (2.0) |
| 50 mM | 46604 | 266492 (5.7) | 140848 (3.0) |
| 10 mM | 64707 | 377231 (5..8) | 187116 (2.9) |
| 1 mM | 92904 | 505437 (5.4) | 281260 (3.0) |

Example 11

Table 15 compares results using the optimum buffer concentration from table 14 (50 mM Bis-Tris Propane (BTP) without surfactants, with 10 mM magnesium acetate, and with recombinant luciferase from PROMEGA at a variety of pH's from pH 6.0 to 9.5. 300 mL of buffer was used with 2.3 uL of 10 mg/mL luciferin and 2.3 uL of 1 mg/mL luciferase. At each pH, both zero results and 0.01 fmol (of ATP-20 uL solution) results are the average of 3 readings. Results show that pH 6.5 provides the optimum signal to noise ratio. Results also show that the signal to noise ratio, using recombinant luciferase, can be improved without maximizing luminescence output by providing a decreased background (noise).

TABLE 15

| pH | 6.0 | 6.5 | 7.0 | 7.5 | 8.0 | 8.5 | 9.0 | 9.5 |
| --- | --- | --- | --- | --- | --- | --- | --- | --- |
| Zero | 24468 | 41531 | 170450 | 240434 | 216444 | 125177 | 114931 | 40990 |
| 0.01 fmol | 33568 | 144012 | 248227 | 451251 | 298006 | 203672 | 161284 | 37106 |
| Pos/Neg ratio | 1.4 | 3.5 | 1.5 | 1.9 | 1.4 | 1.6 | 1.4 | 0.9 |

Example 10

Table 14 shows RLU results using BAR solution of varying millimolar concentrations of Bis-Tris Propane (1 mM-250 mM) pH 6.6 with 0.05% Triton X-100, 0.02% benzalkonium chloride and 10 mM magnesium acetate. The Bis-Tris results are compared with the control of Butterfield's Buffer (0.31 mM monobasic potassium phosphate, pH 7.2) and 0.005% benzalkonium chloride. The signal to noise ratio (positive result/negative result ratio, provided in the parenthesis) of the 50 mM formulation results compared favorably to signal to noise ratio of the 1 mM results and the control. The 50 mM buffer, however, can be more desirable in that it provides better pH stabilization.

Table 16 compares results using the optimum formulation from table 14 (50 mM Bis-Tris Propane (BTP), without surfactants and with 10 mM magnesium acetate, with natural luciferase at a pH range of pH 6.0 to pH 9.5. 300 mL of buffer was used with 2.3 uL 10 mg/mL luciferin and 2.3 uL 1 mg/mL luciferase. At each pH, both zero results and 0.01 fmol (of ATP-20 uL solution) results are the average of 3 readings. Results show that less sensitivity as compared to recombinant luciferase and that, using natural luciferase, at pH 6.5 did not provide as much sensitivity as pH 7.5 and that the maximum signal to noise ratio was achieved at a pH were the luminescence was maximized.

TABLE 16

| pH | 6.0 | 6.5 | 7.0 | 7.5 | 8.0 | 8.5 | 9.0 | 9.5 |
|---|---|---|---|---|---|---|---|---|
| Zero | 28970 | 56213 | 185104 | 205232 | 217513 | 133778 | 53763 | 20586 |
| 0.01 fmol | 27080 | 82236 | 242685 | 379648 | 310669 | 147994 | 70699 | 23529 |
| Pos:neg ratio | 0.9 | 1.5 | 1.3 | 1.8 | 1.4 | 1.1 | 1.3 | 1.1 |

Table 17 compares results using the optimum formulation from table 14 (50 mM Bis-Tris Propane (BTP), without surfactants and with 10 mM magnesium acetate, with recombinant luciferase from PROMEGA at a pH range from pH 6.0 to pH 7.0. 300 mL of buffer was used with 2.3 uL of 10 mg/mL luciferin and 2.3 uL of 1 mg/mL luciferase. At each pH, both zero results and 0.01 fmol (of ATP-20 uL solution) results are the average of 3 readings. Results indicate that at pH 6.5 and pH 6.6 results showed the largest signal to noise ratio.

TABLE 17

| pH | 6.0 | 6.1 | 6.2 | 6.3 | 6.4 | 6.5 |
|---|---|---|---|---|---|---|
| Zero | 56656 | 28352 | 32525 | 38976 | 46390 | 51708 |
| 0.01 fmol | 35307 | 40459 | 59495 | 95783 | 119357 | 156861 |
| Pos:neg ratio | 1.3 | 1.4 | 1.8 | 2.5 | 2.6 | 3.0 |

| pH | 6.6 | 6.7 | 6.8 | 6.9 | 7.0 |
|---|---|---|---|---|---|
| Zero | 65716 | 102317 | 136208 | 161982 | 200930 |
| 0.01 Fmol | 187778 | 232729 | 259382 | 357082 | 382279 |
| Pos:neg Ratio | 2.9 | 2.3 | 1.9 | 2.2 | 1.9 |

Controls for comparison to tables 14-17 included:
1) 50 mM BTP, pH 6.6, with 0.05% Triton X-100, 0.02% benzalkonium chloride. 10 mM magnesium acetate was provided in a solution of 2.3 uL 10 mg/mL luciferin and 2.3 uL 1 mg/mL recombinant luciferase from PROMEGA. Results for blanks (average of 3) were 40376 and results for 0.01 fmol ATP (average of 3) were 160494, for a positive: negative ratio of 4.0. This indicated that the surfactants provided some additional sensitivity at the apparent optimum buffer conditions;
2) 50 mM BTP, pH 6.6, with 0.05% Triton X-100, 0.02% benzalkonium chloride. 10 mM magnesium acetate was provided in a solution of 2.3 uL 10 mg/mL luciferin and 2.3 uL 1 mg/mL natural luciferase. Results for blanks (average of 3) were 111227 and results for 0.01 fmol ATP (average of 3) were 165473, for a positive:negative ratio of 1.5. This confirmed the reduced sensitivity as compared to recombinant luciferase using the apparent optimum conditions for the recombinant reaction. The reduction in sensitivity occurring primarily from the increased negative (background) result; and
3) 50 mM BTP, pH 6.6, with 0.05% Triton X-100, 0.02% benzalkonium chloride. Luciferin/luciferase were provided with magnesium acetate in a tablet, provided within POCKETSWAB PLUS (from Charm Sciences, Inc.) known as the reagent C tablet. Results for blanks (average of 3) were 41222 and results for 0.01 fmol ATP (average of 3) were 164988, for a positive:negative ratio (signal to noise) of 4.0. This confirmed that additional reagent C tablet components were not substantially contributing to the increased sensitivity, as compared to the liquid formulation described above.

Example 12

To determine the optimum range of detergent concentrations varying concentrations of Triton X-100 were tested. Buffer was 50 mM Bis-Tris. Controls included: 50 mM Bis-Tris without detergents and 50 mM Bis-Tris with 0.05% Triton X-100 and 0.02% benzalkonium chloride. Results shown in Table 18 show that although 0.1% Triton X-100 provides the largest difference between positive and negative, the background result (blank result) was relatively high justifying possibly utilizing a lower concentration that did not provide such a large difference between positive and negative but provided a lower background, in this case 0.05% Triton X-100. Results are average of three tests.

TABLE 18

| % Triton X-100 | 0 | 0.001 | 0.005 | 0.01 | 0.05 | 0.1 | 0.25 | 0.5 |
|---|---|---|---|---|---|---|---|---|
| Zero | 31850 | 35786 | 36528 | 38452 | 48708 | 67671 | 96085 | 122869 |
| 0.01 fmol | 102644 | 136453 | 127318 | 140865 | 185585 | 272666 | 353877 | 392306 |
| Pos:neg ratio | 3.2 | 3.8 | 3.5 | 3.7 | 3.8 | 4.0 | 3.7 | 3.2 |

Control results using 50 mM Bis-Tris with 0.05% Triton X-100 and 0.02% benzalkonium chloride were 44658 for negative (background) and 175659 for 0.01 fmol ATP. Results were average of three results.

What is claimed:
1. A method for sensitive detection of ATP in a sample comprising the steps of:
 a) combining a sample to be tested with a solution to create a first admixture;
 b) admixing said first admixture with reagents to form a second admixture, said reagents comprising luciferin and recombinant luciferase, said second admixture comprising at least one buffer wherein a reaction caused by the admixing of said first admixture with said reagents to create said second admixture generates luminescence; and
 c) detecting said generated luminescence as an indication of the presence of ATP in said sample,
wherein the ATP concentration of the second admixture is less than about 3.0 picomolar, and wherein a pH of the second admixture is a pH at which total generated luminescence is below a maximum level and is a pH at which a signal to noise ratio is maximized.

2. The method of claim 1 wherein the ATP concentration of the second admixture is about 2.0 picomolar to about 3.0 picomolar.

3. The method of claim 1 wherein the ATP concentration of the second admixture is about 1.0 picomolar to about 2.0 picomolar.

4. The method of claim 1 wherein the ATP concentration of the second admixture is less than about 1.0 picomolar.

5. The method of claim 1 wherein the recombinant luciferase is expressed using a recombinant DNA derived from a Coleoptera.

6. A method for sensitive detection of ATP in a sample comprising the steps of:
   a) combining a sample to be tested with a solution to create a first admixture;
   b) admixing said first admixture with reagents to form a second admixture, said reagents comprising luciferin and Coleoptera luciferase, said second admixture comprising at least one buffer wherein a reaction caused by the admixing of said first admixture with said reagents to create said second admixture generates luminescence; and
   c) detecting said generated luminescence as an indication of the presence of ATP in said sample,
wherein the ATP concentration of the second admixture is less than about 3.4 picomolar, and wherein a pH of the second admixture is a pH at which total generated luminescence is below a maximum level and is a pH at which a signal to noise ratio is maximized.

7. The method of claim 6 wherein the ATP concentration of the second admixture is about 3.0 picomolar to about 3.4 picomolar.

8. The method of claim 6 wherein the ATP concentration of the second admixture is about 2.0 picomolar to about 3.0 picomolar.

9. The method of claim 6 wherein the ATP concentration of the second admixture is about 1.0 picomolar to about 2.0 picomolar.

10. The method of claim 6 wherein the ATP concentration of the second admixture is less than about 1.0 picomolar.

11. The method of claim 6 wherein said solution further comprises at least one detergent.

12. The method of claim 6 wherein the detecting of generated luminescence comprises measuring sample luminescence with a luminometer, said luminometer comprising a photomultiplier tube, and wherein the total luminescence generated, during a predetermined period of time, is measured and used as the indication of the presence of ATP in said sample.

13. The method of claim 12 wherein the detecting of generated luminescence comprises measuring the total luminescence generated, during a predetermined period of time, and wherein said total luminescence is used to predict the total luminescence that would be generated over a period of time longer than said predetermined period of time and wherein said predicted total luminescence is used as an indication of the presence of ATP in the sample.

14. The method of claim 6 wherein the Coleoptera luciferase is expressed using a recombinant DNA derived from a Coleoptera.

15. The method of claim 6 wherein said luciferin comprises a Coleoptera luciferin.

16. The method of claim 6 wherein said Coleoptera, luciferase is expressed using a recombinant DNA derived from a Coleoptera and said luciferin comprises a Coleoptera luciferin.

17. The method of claim 6 wherein said Coleoptera luciferase comprises luciferase of an insect selected from the families Lampyridae and Elateridae.

18. The method of claim 6 wherein said Coleoptera luciferase comprises luciferase of an insect selected from the genus *Photinus*.

19. The method of claim 6 wherein said Coleoptera luciferase comprises luciferase of the species *Photinus pyralis*.

20. The method of claim 6 wherein said Coleoptera luciferase comprises luciferase of an insect from the Diptera family.

* * * * *